United States Patent
Vauzeilles et al.

(10) Patent No.: US 10,640,526 B2
(45) Date of Patent: May 5, 2020

(54) METHOD OF PREPARATION OF 6-AZIDO-2,4-DIACETAMIDO-2,4,6-TRIDEOXY-D-MANNOSE

(71) Applicant: Centre national de la recherche scientifique, Paris (FR)

(72) Inventors: Boris Vauzeilles, Sceaux (FR); Aurélie Baron, L'Isle Adam (FR); Jordi Mas Pons, Barecelone (ES); Laura Fourmois, Buchelay (FR)

(73) Assignee: CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 0 days.

(21) Appl. No.: 15/777,067

(22) PCT Filed: Nov. 16, 2016

(86) PCT No.: PCT/EP2016/077901
§ 371 (c)(1),
(2) Date: May 17, 2018

(87) PCT Pub. No.: WO2017/085145
PCT Pub. Date: May 26, 2017

(65) Prior Publication Data
US 2018/0319833 A1   Nov. 8, 2018

(30) Foreign Application Priority Data
Nov. 17, 2015 (EP) .................... 15306825

(51) Int. Cl.
*C07H 5/04* (2006.01)
*C07H 13/04* (2006.01)
*C07H 23/00* (2006.01)
*C07H 1/00* (2006.01)
*C12Q 1/04* (2006.01)

(52) U.S. Cl.
CPC ............ *C07H 5/04* (2013.01); *C07H 1/00* (2013.01); *C07H 13/04* (2013.01); *C07H 23/00* (2013.01); *C12Q 1/04* (2013.01)

(58) Field of Classification Search
None
See application file for complete search history.

(56) References Cited

FOREIGN PATENT DOCUMENTS

| WO | 02/062810 A2 | 8/2002 |
| WO | 2013/107759 A1 | 7/2013 |
| WO | 2015/063173 A1 | 5/2015 |

OTHER PUBLICATIONS

Feng Liu et al: "The Engineering of Bacteria Bearing Azido-Pseudaminic Acid-Modified Flagella", Chembiochem, vol. 10, No. 8, May 25, 2009 (May 25, 2009), pp. 1317-1320, XP055090380, ISSN: 1439-4227, DOI: 10.1002/cbic.200900018.

Yi Qiu et al: "Synthetic Studies on Polysaccharide HS-142-1, a Novel Nonpeptide Antagonist for the Atrial Natriuretic Peptide Receptor: Syntheses of the Gentiobiosyl Fragments", Bioscience Biotechnology Biochemistry., vol. 60, No. 6, Jan. 12, 1996 (Jan. 12, 1996), Tokyo, Japan, pp. 986-993, XP055248171, ISSN: 0916-8451, DOI: 10.1271/bbb.60.986.

Zhang Z et al: "Regioselective benzoylation of sugars mediated by excessive Bu2SnO: observation of temperature promoted migration", Tetrahedron, Elsevier Science Publishers, Amsterdam, NL, vol. 58, No. 32, Aug. 5, 2002 (Aug. 5, 2002), pp. 6513-6519, XP004374091, ISSN: 0040-4020, DOI: 10.1016/S0040-4020(02)00661-0.

Kolb H C: "Design and synthesis of a macrocyclic e-selectin antagonist", Bioorganic & Medicinal Chemistry Letters, Pergamon, Amsterdam, NL, vol. 7, No. 20, Oct. 21, 1997 (Oct. 21, 1997), pp. 2629-2634, XP004136501, ISSN: 0960-894X, DOI: 10.1016/S0960-894X(97)10041-5.

Chiara J L et al: "A study of polymer-supported bases for the solution phase synthesis of glycosyl trichloroacetimidates", Tetrahedron Letters, Elsevier, Amsterdam, NL, vol. 46, No. 14, Apr. 4, 2005 (Apr. 4, 2005), pp. 2445-2448, XP027863153, ISSN: 0040-4039, [retrieved on Apr. 4, 2005].

E. Durantie et al. Fluorine-Directed b-Galactosylation: Chemical Glycosylation Development by Molecular Editing ., vol. 18, 2012, pp. 8208-8215.

C. Huo et al.,Stereoselective Synthesis of Natural N-(1-Deoxy-D-β-fructos-1-yl)-L-amino Acids and Their Effect on Lead Decorporation Chem. Res. Toxicol., vol. 17, No. 8, 2004, pp. 1112-1120.

K. Jansson et al. "2-Trimethylsilylethyl Glycosides* Anomeric Deblocking of Mono and Disaccharides"., vol. 29, 1988, pp. 361-362.

(Continued)

*Primary Examiner* — Layla D Berry
(74) *Attorney, Agent, or Firm* — Young & Thompson

(57) ABSTRACT

Disclosed is a method of preparation of 6-azido-2,4-diacetamido-2,4,6-trideoxy-D-mannose. This method includes the chemical reaction of compound of formula X:

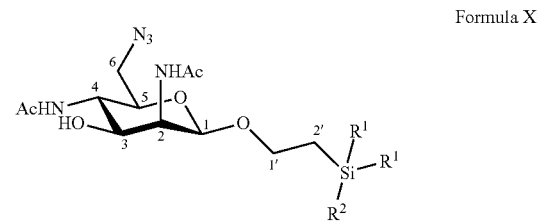

Formula X

Wherein: $R^1$ can be a $C_1$ to $C_6$ alkyl including methyl, ethyl, isopropyl; aryl including phenyl; each of these groups being substituted or not; and $R^2$ can be a $C_1$ to $C_6$ alkyl including methyl, ethyl, isopropyl, tert-butyl, isobutyl; each of these groups being substituted or not; with a deprotecting reagent including a Lewis or Brönsted acid in a polar aprotic solvent, thereby obtaining a free C-1 OH group. The method can also start with the preparation from commercially available D-galactose pentaacetate, D-galactose tetraacetate or tetraacetyl D-galactosyl trichloroacetimidate. The step of deprotecting the anomeric position avoids the use of cerium and allows the easy purification of 6-azido-2,4-diacetamido-2,4,6-trideoxy-D-mannose.

20 Claims, No Drawings

(56) References Cited

OTHER PUBLICATIONS

D. Lee; M. S. Taylor, J. Am. "Borinic Acid-Catalyzed Regioselective Acylation of Carbohydrate Derivatives" Chem. Soc., vol. 133, 2011, pp. 3724-3727.

J. Mas Pons et al. "Identification of Living Legionella pneumophila Using Species-Specific Metabolic Lipopolysaccharide Labeling" Chem. Int ED., vol. 53, 2014, pp. 1275-1278.

W. Pilgrim et al. "SnCl4- and TiCl4-Catalyzed Anomerization of Acylated O- and S-Glycosides: Analysis of Factors That Lead to Higher r:β Anomer Ratios and Reaction Rates" Chem., vol. 75, 2010, pp. 6747-6755.

J. J. Plattner et al. "Synthesis of Some DE and CDE Ring Analogs of Camptothecin". Chem. Soc., vol. 94, 1972, pp. 8613.

Y. E. Tsvetkov et al. "Synthesis and NMR spectroscopy of nine stereoisomeric 5,7-diacetamido-3,5,7,9- tetradeoxynon-2-ulosonic acids" vol. 335, 2001, pp. 221-243.

EP Search Report, dated Feb. 8, 2016, from corresponding EP15 30 6825 application.

International Search Report, dated Jan. 23, 2017, from corresponding PCT/EP2016/077901 application.

METHOD OF PREPARATION OF 6-AZIDO-2,4-DIACETAMIDO-2,4,6-TRIDEOXY-D-MANNOSE

INTRODUCTION

The invention relates to the preparation of known 6-azido-2,4-diacetamido-2,4,6-trideoxy-D-mannose ("Man2NAc4NAc6N$_3$") by a new synthesis route with excellent purity and easy purification steps by avoiding the use of contaminating metals highly difficult to eliminate like cerium. In a best particular mode, the synthesis starts from a commercially available galactose derivative, for instance commercially available D-galactose pentaacetate, D-galactose tetraacetate or tetraacetyl D-galactosyl trichloroacetimidate. The product of interest 11 is obtained from β-D-galactose pentaacetate with an overall yield of 8 mol % and a purity of more than 95% by NMR analysis.

The invention further relates to synthesis intermediates, which are claimed as new compounds, selected from the group consisting of compounds of formulae V, VI, VIII, IX, X. More precisely, the invention further relates to specific synthesis intermediates, which are claimed as new compounds, selected from the group consisting of compounds 5, 6, 8, 9 and 10, set forth here-below.

DISCUSSION OF PRIOR ART

Dumont et al. in WO 2013/107759, and *Angew. Chem. Int. Ed.*, 2012, 51, P3143-3146, and *Angew. Chem.*, 2012, 124, P3197-3200 have previously shown that metabolic glycan labelling, in which a modified monosaccharide bearing a reporter function is metabolically incorporated into surface glycans, could be efficiently used to target bacterial LPS (LipoPolySaccharides) without species specificity. In this first study, an azido derivative of Kdo, a bacterial monosaccharide, was incorporated into the LPS inner core of various Gram-negative bacteria, thereby allowing to detect the bacteria by a so-called click chemistry.

Then, Mas Pons et al. ("Mas"), including the present Inventors, in WO 2015/063173 and publication *Angew. Chem. Int. Ed.*, 2014, 53, P1275-1278 and *Angew. Chem.*, 2014, 126, P1299-1302, have improved the Dumont route by using metabolic LPS labelling to identify living pathogenic bacteria of interest in the sample by using an analogue of a monosaccharide which will be specifically present within the O-antigen of these bacteria.

Thus, Mas Pons et al. relates to the identification of living *Legionella pneumophila* using species-specific metabolic LPS labeling.

Mas mentions that the O-antigen of *L. pneumophila* serogroup 1, which is prevalent among infected cases, is composed of an α(2-4)homopolysaccharidic repeat of 5-N-acetamidoyl-7-N-acetyl-legionaminic acid named in abbreviation Leg5Am7Ac ("Leg"). The biosynthesis of Leg starts from UDP-N,N'-diactetylbacillosamine, which is transformed into 2,4-diacetamido-2,4,6,-trideoxy-D-mannopyranose ("Mannose 1") by the dual action of a hydrolysing 2-epimerase. Then, the precursor is directly transformed into N,N-diacetyl-legionaminic acid (Leg5Ac7Ac) in the presence of phosphoenolpyruvate (PEP) by the action of an aldolase which controls the stereochemistry of the newly generated stereogenic center at C-4. Legionaminic acid is then activated in the form of a cytidine monophosphate donor (CMP)'-Leg5Ac7Ac, further transformations being believed to occur at a later stage.

Mas more precisely targets the Leg pathway for metabolic glycan labelling. Thus, Mas relates to the synthesis of an azido derivative of Mannose 1, namely 6-azido-2,4-diacetamido-2,4,6-trideoxy-D-mannopyranose numbered 2 on FIG. 1 of Mas (also named "6-azido Mannose 2" or "Man2NAc4NAc6N$_3$") as well as its less polar monoacetylated derivative numbered 3, which was believed by Mas to enter more easily in the cell by passive transport and be further transformed into the 6-azido Mannose 2.

Once in the cell, the 6-azido Mannose 2 was believed by Mas to act as a precursor of an azido-labelled analog of legionaminic acid further incorporated into the O-antigen of the bacteria. Then, this Leg analog is detected according to the click chemistry method well known to one skilled in the art.

The originality of Mas was the use of an azido (N$_3$) analog of the compound 1 which is converted into a Leg analog, itself incorporated in the bacterial LPS.

With regard to the synthesis route, Mas developed a strategy starting from D-galactose to access compounds 2 and 3 cited above and reported on FIG. 1 of Mas.

The target compound 2 was synthetized in eleven steps starting from the commercially available β-D-galactose pentaacetate with an overall yield of 17 mol % while the compound 3 was obtained from the same starting material in twelve steps with an overall yield of 15 mol %.

The last synthesis step to reach the compound 2 with a good yield of 82 mol % by deprotection of the anomeric position, required using cerium ammonium nitrate. Compound 3 was obtained with similar conditions.

However in Mas synthesis, the drawback is that the selective deprotection of the preceding intermediate protected by a ParaMethoxyPhenyl or PMP group requires the use of a cerium inorganic salt which is highly difficult to remove from the reaction medium. To eliminate the cerium, it is necessary to perform several purifying steps implying difficult and poorly reproducible chromatographies, and in addition, by the end, it often still remains traces of cerium which can show toxicity to the target cell or organism.

The cerium contaminated product cannot be marketed.

WO 2015/063173 describes on page 40, compound 1 which is 2,4-diazido-2,4-dideoxy-D-mannose having in position 1 an —OSE substituent wherein OSE means O-trimethyl-SilylEthyl corresponding to synthesis intermediate 7 described farther in the invention synthesis scheme.

YI QIYU et al. in *BioScience Biotech. Biochem.*, 60, (6), 986-993, 1996, relates to the synthetic studies on Polysaccharide HS-142-1 with the provision of possible disaccharide fragments. YI QIYU discloses on scheme 1, Page 987, a monosaccharide compound 18 which is different from the invention compounds by having a glucose configuration whereas the invention relates to a galactose configuration.

ZHANG et al. in *Tetrahedron*, 58, 2002, 6513-6519, relates to regioselective benzoylation of sugars mediated by excessive Bu$_2$SnO. Compound 15 disclosed on page 6514 is different from the invention since it bears a substituent —N$_3$ in position 2 contrary to what is mentioned under table 1, whereas the invention closest compound bears two substituents OH in position 2 and 4, which completely changes the selectivity of this step.

Problems to be Solved by the Invention

A main aim of the present invention lies in solving the technical problem of finding a new method of synthesis for arriving to the Leg precursor analog without using cerium.

Another main aim of the present invention lies in solving this technical problem according to a technical solution which is reliable and reproducible at the industrial scale.

A further aim of the invention is to prepare the Leg precursor analog from commercial D-galactose derivative.

The invention method solves this technical problem by providing a new synthesis route which reaches this Leg precursor analog with much less numerous and much easier and reproducible purification steps, preferably with a reversed phase chromatography. Moreover, the final product is devoid of toxic cerium salts since no cerium is used in the overall synthetic sequence.

The new synthetic route can more easily be performed on a higher scale.

A further aim of the invention is to provide new synthesis intermediate compounds.

SUMMARY OF THE INVENTION

The above technical problems are solved by the invention as defined by the claims.

In the description and claims, the abbreviations have their usual meaning known to one skilled in the chemical art. For instance:

Ac is for Acetyl; Bz is for Benzoyl; Me is for Methyl; Ms is for Methanesulfonyl;

Man2NAc4NAc6N$_3$ is for 6-azido-2,4-diacetamido-2,4,6-trideoxy-D-mannose.

According to a first aspect the invention relates to a method of preparation of the specific compound 11, named 6-azido-2,4-diacetamido-2,4,6-trideoxy-D-mannose, here-below:

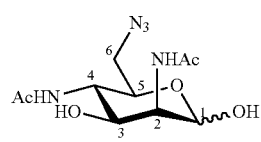

Compound 11 comprising the chemical reaction of compound of formula X:

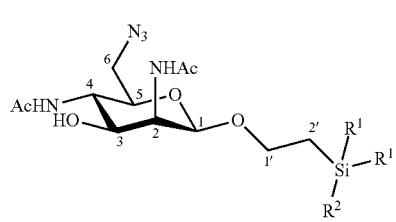

Formula X

Wherein:

R$^1$ can be a C$_1$ to C$_6$ alkyl including methyl, ethyl, isopropyl; aryl including phenyl; each of these groups being substituted or not;

and R$^2$ can be a C$_1$ to C$_6$ alkyl including methyl, ethyl, isopropyl, tert-butyl, isobutyl; each of these groups being substituted or not;

with a deprotecting reagent comprising a Lewis or Brönsted acid in a polar aprotic solvent, thereby obtaining a free C-1 OH group.

According to a particular feature, the product of interest 11 could be obtained from compound of formula X (10 mg to 50 g), by deprotection of the anomeric protected group by the use of a Lewis or Brönsted acid (1 to 400 equivalents), such as trifluoroacetic acid, boron trifluoride diethyletherate, more particularly trifluoroacetic acid, in a polar aprotic solvent, such as chloroform, dichloromethane, tetrahydrofuran, ethyl acetate, acetone, N,N-dimethylformamide, acetonitrile, dimethylsulfoxide (0.01 to 0.50 M), typically dichloromethane, at a temperature between −30 and 100° C. The reaction mixture can be purified by any means including chromatography over reversed-phase C18 silica.

More particularly, the invention relates to a method of preparation of the specific compound 11, comprising the chemical reaction of compound 10, named 1'-trimethylsilylethanyl 6-azido-2,4-diacetamido-2,4,6-trideoxy-β-D-mannopyranoside, here-below:

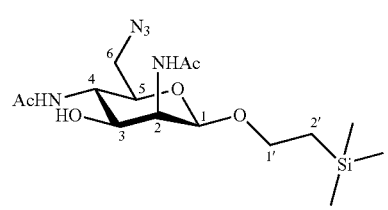

Compound 10 under the above same reaction conditions.

This deprotecting step was not obvious for one skilled in the art in view of the following facts:

1—risk of degradation of the product since the reacting conditions are strongly acidic;

2—risk of elimination of HN$_3$ which would lead to the formation of an alkene function and the possible degradation of the product.

3—possibility of formation of an oxazoline derivative.

4—the usual conditions for this deprotection use BF$_3$—OEt$_2$ which work well on some apolar derivatives but which were unefficient on this step.

According to a particular embodiment, the invention relates to a method of preparation of synthesis intermediate compound of formula X, comprising the chemical reaction of a compound of formula IX:

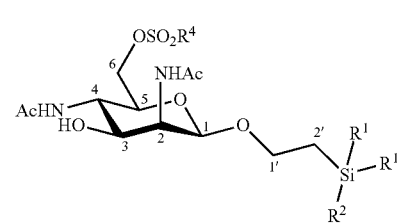

Formula IX

Wherein:

R$^1$ can be a C$_1$ to C$_6$ alkyl including methyl, ethyl, isopropyl; aryl including phenyl; each of these groups being substituted or not;

and R$^2$ can be a C$_1$ to C$_6$ alkyl including methyl, ethyl, isopropyl, tert-butyl, isobutyl; each of these groups being substituted or not;

and R$^4$ can be a C$_1$ to C$_6$ alkyl including methyl, ethyl, propyl; C$_1$ to C$_6$ perfluoroalkyl including trifluoromethyl, pentafluoroethyl; or aryl including para-methylphenyl, para-nitrophenyl; each of these groups being substituted or not;

with an azide formation reagent comprising an organic or inorganic azide salt in a non-polar solvent or in a polar aprotic solvent, thereby obtaining a 6-azido group.

According to a particular feature, compound of formula X could be obtained by reaction of compound of formula IX (10 mg to 100 g) and an organic or inorganic azide salt (0.8 to 15.0 equivalents) such as sodium azide, lithium azide, tetra-n-butylammonium azide, preferably sodium azide, in a non-polar solvent such as pentane, hexane, cyclohexane, benzene, toluene, chloroform, diethyl ether, dioxane, or in a polar aprotic solvent (0.01 to 0.50 M), such as chloroform, dichloromethane, tetrahydrofuran, ethyl acetate, acetone, N,N-dimethylformamide, acetonitrile, dimethylsulfoxide, typically N,N-dimethylformamide, at a temperature between 0 and 150° C.

More particularly, the invention relates to a method of preparation of the specific synthesis intermediate compound 10, comprising the chemical reaction of compound 9, named 1'-trimethylsilylethanyl 2,4-diacetamido-2,4-dideoxy-6-O-mesyl-β-D-mannopyranoside, here-below:

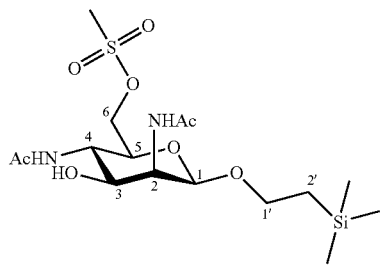

Compound 9 under the above same reaction conditions as for the preparation of compound X.

This synthesis step was also not obvious for one skilled in the art since the transformation of the mesylate into an azido function could also be problematic. Indeed, the change of protecting group in position 1 by a less hindering and more flexible group could increase the proportion of bicyclic by-product, through an attack of OH in position 3 onto the mesylate.

According to another particular embodiment, the invention relates to a method of preparation of synthesis intermediate compound of formula IX, comprising the chemical reaction of compound of formula VIII:

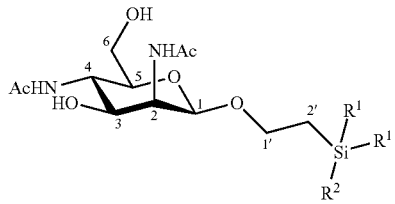

Formula VIII

Wherein:
$R^1$ can be a $C_1$ to $C_6$ alkyl including methyl, ethyl, isopropyl; aryl including phenyl; each of these groups being substituted or not;
and $R^2$ can be a $C_1$ to $C_6$ alkyl including methyl, ethyl, ethyl, isopropyl, tert-butyl, isobutyl; each of these groups being substituted or not;
with a sulfonyl chloride or sulfonic anhydride in the presence of a base, with or without an organic solvent.

According to a particular feature, compound of formula IX could be obtained from compound of formula VIII (20 mg to 100 g) by reaction with a sulfonyl chloride or sulfonic anhydride (0.8 to 3.0 equivalents), such as mesyl chloride, tosyl chloride, nosyl chloride or trifluoromethanesulfonyl anhydride, preferably mesyl chloride, in the presence of an organic base (0.8 to 200 equivalents) such as pyridine, triethylamine, diisopropylethylamine, typically pyridine, with or without a polar aprotic solvent (0.01 to 0.50 M) such as chloroform, dichloromethane, tetrahydrofuran, ethyl acetate, acetone, N,N-dimethylformamide, acetonitrile, dimethylsulfoxide, at a temperature between −30 and 100° C.

More particularly, the invention relates to a method of preparation of the specific synthesis intermediate compound 9, comprising the chemical reaction of compound 8, named 1'-trimethylsilylethanyl 2,4-diacetamido-2,4-dideoxy-β-D-mannopyranoside, here-below:

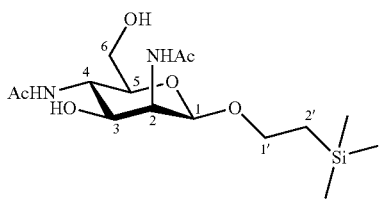

Compound 8 under the above same reaction conditions as for the preparation of compound IX.

This sulfonylation step was also not obvious for one skilled in the art since, the change of protecting group in position 1 by a less hindering and more flexible group could provide a negative effect on the selectivity in position 6. This change of protecting group could also influence the reactivity on position 3 and result in the formation of a higher proportion of, for example, di-mesylated derivative under the excess of mesyl chloride.

According to another particular embodiment, the invention relates to a method of preparation of the specific synthesis intermediate compound of formula VIII, comprising the chemical reaction of compound of formula VII:

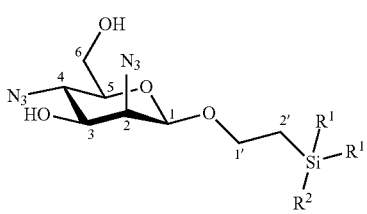

Formula VII

Wherein:
$R^1$ can be a $C_1$ to $C_6$ alkyl including methyl, ethyl, isopropyl; aryl including phenyl; each of these groups being substituted or not;
and $R^2$ can be a $C_1$ to $C_6$ alkyl including methyl, ethyl, isopropyl, tert-butyl, isobutyl; each of these groups being substituted or not;
in a protic solvent, with a reagent for the reduction of azido groups. Then the intermediate product obtained is reacted with an acylating reagent.

According to a particular feature, compound of formula VIII could be obtained from compound of formula VII (20 mg to 100 g) by reduction of the azido groups into amino groups using classical conditions such as triphenylphosphine, indium, hydrogen sulphide, a thiol or dithiol, lithium aluminium hydride, sodium borohydride, palladium on charcoal with an hydrogen source, more particularly a catalytic amount of palladium hydroxide on charcoal with an hydrogen atmosphere, in a polar protic solvent, such as tert-butanol, n-propanol, isopropanol, ethanol, methanol or mixture of polar protic and aprotic solvents, such as tert-butanol, n-propanol, isopropanol, ethanol, methanol or water, and chloroform, dichloromethane, tetrahydrofuran, ethyl acetate, acetone, N,N-dimethylformamide, acetonitrile, dimethylsulfoxide, (0.01 to 0.50 M), potentially in the presence of an added acid such as acetic acid or hydrochloric acid, preferably methanol, at a temperature between 0 and 100° C. Then both amino groups could react with an activated acetic acid (1.5 to 15 equivalents) such as acetyl chloride, acetic anhydride, or in the presence of acetic acid and a classical coupling reagent for peptide synthesis, more particularly acetic anhydride, in a protic solvent (0.01 to 0.50 M) such as tert-butanol, n-propanol, isopropanol, ethanol, methanol, preferably methanol, or in a polar aprotic solvent, such as chloroform, dichloromethane, tetrahydrofuran, ethyl acetate, acetone, N,N-dimethylformamide, acetonitrile, dimethylsulfoxide, typically N,N-dimethylformamide, at a temperature between −15 and 50° C.

More particularly, the invention relates to a method of preparation of the specific synthesis intermediate compound 8, comprising the chemical reaction of compound 7, named 1'-trimethylsilylethanyl 2,4-diazido-2,4-dideoxy-β-D-mannopyranoside, here-below:

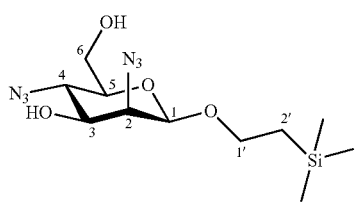

Compound 7 under the above same reaction conditions as for the preparation of compound VIII.

According to a further particular embodiment, the invention relates to a method of preparation of synthesis intermediate compound of formula VII, comprising the chemical reaction of compound of formula VI:

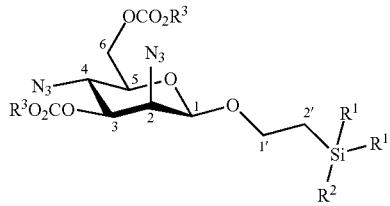

Formula VI

Wherein:
$R^1$ can be a $C_1$ to $C_6$ alkyl including methyl, ethyl, isopropyl; aryl including phenyl; each of these groups being substituted or not;

and $R^2$ can be a $C_1$ to $C_6$ alkyl including methyl, ethyl, isopropyl, tert-butyl, isobutyl; each of these groups being substituted or not;

and $R^3$ can be a $C_1$ to $C_6$ alkyl including methyl, ethyl, propyl, butyl, t-butyl; aryl including phenyl, para-methoxyphenyl; each of these groups being substituted or not;

in a protic solvent by using a classical reagent for deprotection of ester groups.

According to a particular feature, compound of formula VII could be obtained from compound of formula VI (50 mg to 100 g) by deprotection of ester groups at the 3 and 6 positions by action of classical reagents such as sodium methanolate or potassium carbonate (0.05 to 10.0 equivalents) in a protic solvent (0.01 to 0.50 M) such as tert-butanol, n-propanol, isopropanol, ethanol, methanol, typically methanol, at a temperature between −10 and 50° C.

More particularly, the invention relates to a method of preparation of the specific synthesis intermediate compound 7, comprising the chemical reaction of compound 6, named 1'-trimethylsilylethanyl 2,4-diazido-2,4-dideoxy-3,6-di-O-benzoyl-β-D-mannopyranoside, here-below:

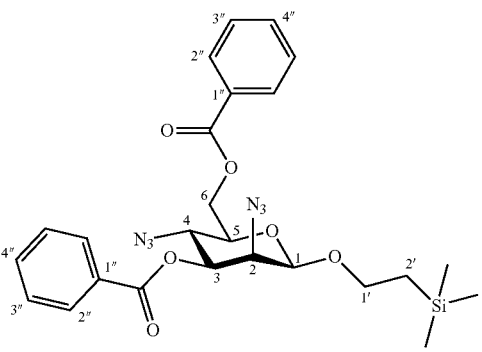

Compound 6 under the above same reaction conditions as for the preparation of compound VII.

According to another particular embodiment, the invention relates to a method of preparation of synthesis intermediate compound of formula VI, comprising the chemical reaction of compound of formula V:

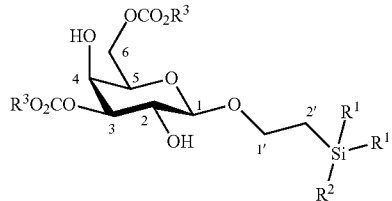

Formula V

Wherein:
$R^1$ can be a $C_1$ to $C_6$ alkyl including methyl, ethyl, isopropyl; aryl including phenyl; each of these groups being substituted or not;

and $R^2$ can be a $C_1$ to $C_6$ alkyl including methyl, ethyl, isopropyl, tert-butyl, isobutyl; each of these groups being substituted or not;

and $R^3$ can be a $C_1$ to $C_6$ alkyl including methyl, ethyl, propyl, butyl, t-butyl; aryl including phenyl, para-methoxyphenyl; each of these groups being substituted or not;

with an azido providing reagent, after adding to the organic solution, sulfonyl chloride or sulfonic anhydride in presence of a base in a polar aprotic solvent.

According to a particular feature, compound of formula VI could be obtained from compound of formula V (50 mg to 100 g) by reaction with a sulfonyl chloride or sulfonic anhydride (1.5 to 6.0 equivalents), such as mesyl chloride, tosyl chloride, nosyl chloride or trifluoromethanesulfonic anhydride, typically trifluoromethanesulfonic anhydride, in the presence of an organic base (1.0 to 200 equivalents) such as pyridine, triethylamine, diisopropylethylamine, typically pyridine, in a polar aprotic solvent (0.01 to 0.50 M) such as chloroform, dichloromethane, tetrahydrofuran, ethyl acetate, acetone, N,N-dimethylformamide, acetonitrile, dimethylsulfoxide, typically dichloromethane, at a temperature between −30 and 100° C. Then the activated derivative could react with an organic or inorganic azide salt (1.5 to 50 equivalents) such as sodium azide, lithium azide, tetrabutylammonium azide, preferably tetra-n-butylammonium azide, in a polar aprotic solvent such as chloroform, dichloromethane, tetrahydrofuran, ethyl acetate, acetone, N,N-dimethylformamide, acetonitrile, dimethylsulfoxide, or in a non-polar solvent (0.01 to 0.50 M) such as pentane, hexane, cyclohexane, benzene, toluene, chloroform, diethyl ether, dioxane, typically toluene, at a temperature between 0 and 160° C.

More particularly, the invention relates to a method of preparation of the specific synthesis intermediate compound 6, comprising the chemical reaction of compound 5, named 1'-trimethylsilylethanyl 3,6-di-O-benzoyl-β-D-galactopyranoside, here-below:

Compound 5

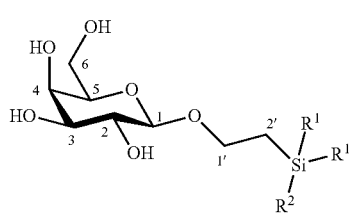

under the above same reaction conditions as for the preparation of compound VI.

According to another particular embodiment, the invention relates to a method of preparation of synthesis intermediate compound of formula V, comprising the chemical reaction of compound of formula IV:

Formula IV

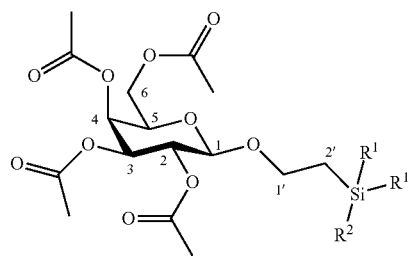

Wherein
$R^1$ can be a $C_1$ to $C_6$ alkyl including methyl, ethyl, isopropyl; aryl including phenyl; each of these groups being substituted or not;
and $R^2$ can be a $C_1$ to $C_6$ alkyl including methyl, ethyl, isopropyl, tertbutyl, isobutyl; each of these groups being substituted or not;
with 2-aminoethyl diphenylborinate or bis(tributyltin)oxide and an acyl chloride in a polar aprotic solvent in the presence of a base.

According to a particular feature, compound of formula V could be obtained from compound of formula IV (20 mg to 100 g) by selective protection of hydroxyl groups at the 3 and 6 positions with acyl chloride (1.5 to 6 equivalents) such as acetyl chloride, benzoyl chloride or substituted benzoyl chloride, more particularly benzoyl chloride, in the presence of an organic base (1.5 to 6 equivalents) such as pyridine, triethylamine, diisopropylethylamine, typically N,N-diisopropylethylamine, and a catalyst (0.05 to 0.5 equivalents), preferably 2-aminoethyl diphenylborinate, in a polar aprotic solvent (0.01 to 0.50 M), such as dichloromethane, tetrahydrofuran, ethyl acetate, acetone, N,N-dimethylformamide, acetonitrile, dimethylsulfoxide, typically acetonitrile, at a temperature between −30 and 150° C., or after preactivation of 4 in the form of a bis stannyl ether, using $(Bu_3Sn_2)_2O$.

More particularly, the invention relates to a method of preparation of the specific synthesis intermediate compound 5, comprising the chemical reaction of compound 4, named 1'-trimethylsilylethanyl β-D-galactopyranoside, here-below:

Compound 4

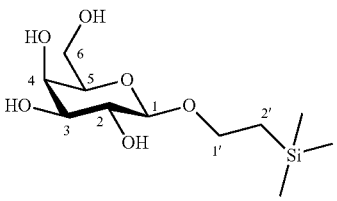

under the above same reaction conditions as for the preparation of compound V.

According to another particular embodiment, the invention relates to a method of preparation of synthesis intermediate compound of formula IV, comprising the chemical reaction of compound of formula III:

Formula III

Wherein:
$R^1$ can be a $C_1$ to $C_6$ alkyl including methyl, ethyl, isopropyl; aryl including phenyl; each of these groups being substituted or not;
and $R^2$ can be a $C_1$ to $C_6$ alkyl including methyl, ethyl, isopropyl, tert-butyl, isobutyl; each of these groups being substituted or not;

in a protic solvent, in the presence of a classical reagent for the deprotection of ester groups.

According to a particular feature, compound of formula IV could be obtained from compound of formula III (50 mg to 100 g) by deprotection of ester groups by action of classical reagents such as sodium methanolate or potassium carbonate (0.05 to 10.0 equivalents) in a protic organic solvent (0.01 to 0.50 M) such as tert-butanol, n-propanol, isopropanol, ethanol, methanol, typically methanol, at a temperature between −10 and 50° C.

More particularly, the invention relates to a method of preparation of the specific synthesis intermediate compound 4, comprising the chemical reaction of compound 3, named 1'-trimethylsilylethanyl (OSE) 2,3,4,6-tetra-O-acetyl-β-D-galactopyranoside, here-below:

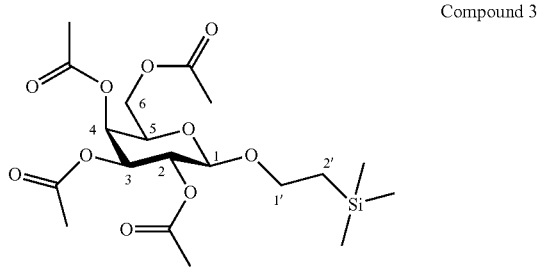

Compound 3 under the above same reaction conditions as for the preparation of compound IV.

According to another particular embodiment, the invention relates to a method of preparation of synthesis intermediate compound of formula III or of compound 3, comprising the chemical reaction of compound 2, named O-(2,3,4,6-tetra-O-acetyl-β-D-galactopyranosyl) trichloroacetimidate, here-below:

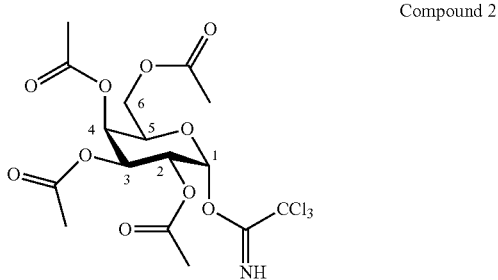

Compound 2 with a primary alcohol bearing a silyl group in the presence of a Lewis acid in a polar aprotic solvent.

According to a particular feature, compound of formula III or of compound 3 could be obtained from compound 2 (50 mg to 100 g) by reaction with a primary alcohol bearing a silyl group (0.5 to 5.0 equivalents) such as trimethylsilylethanol, triethylsilylethanol, triisopropylsilylethanol, dimethylisopropylsilylethanol, tert-butyldimethylsilylethanol, tert-butyldiphenylsilylethanol, more preferably trimethylsilylethanol, in the presence of a Lewis or Brönsted acid (0.01 to 5.0 equivalent) such as trimethylsilyl trifluoromethanesulfonate, boron trifluoride diethyletherate, trifluoromethanesulfonic acid, triethylsilyl trifluoromethanesulfonate, tert-butyldimethylsilyl trifluoromethanesulfonate, typically trimethylsilyl trifluoromethanesulfonate, in a polar aprotic solvent (0.01 to 0.50 M) such as chloroform, dichloromethane, tetrahydrofuran, ethyl acetate, acetone, N,N-dimethylformamide, acetonitrile, dimethylsulfoxide, more preferably dichloromethane, at a temperature between −78 and 50° C.

According to another particular embodiment, the invention relates to a method of preparation of specific synthesis intermediate compound 2, comprising the chemical reaction of compound 1, named 2,3,4,6-tetra-O-acetyl-D-galactopyranose, here-below:

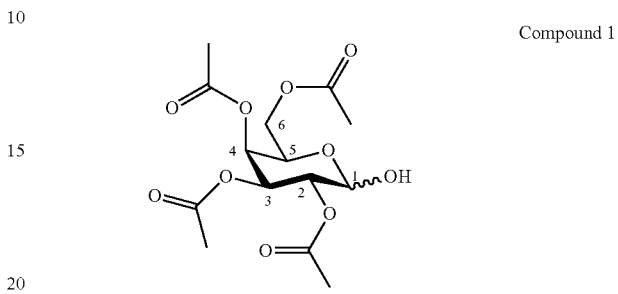

Compound 1 with an imidate introducing reagent in the presence of a base in a polar aprotic solvent.

According to a particular feature, compound 2 could be obtained from compound 1 (50 mg to 100 g) by reaction with trichloroacetonitrile (1.0 to 100.0 equivalents) in presence of an organic or inorganic base (0.01 to 10.0 equivalents), typically 1,8-diazabicyclo(5.4.0)undec-7-ene, potassium carbonate, sodium hydride, cesium carbonate, more preferably 1,8-diazabicyclo(5.4.0)undec-7-ene, in a polar aprotic solvent (0.01 to 0.50 M), such as chloroform, dichloromethane, tetrahydrofuran, ethyl acetate, acetone, N,N-dimethylformamide, acetonitrile, dimethylsulfoxide, preferably dichloromethane, at a temperature between −40 and 50° C.

It is apparent from the above that the preparation of compound III or 3 in three steps from compound 1 galactose penta-acetate was not obvious for one skilled in the art since one step methods exist enabling the obtention of the per-acetyated OSE derivative. See for example, *J. Org. Chem.*, 1998, 53, 5629-5647 and *Bioorg. Med. Chem. Lett.*, 2006, 16, 5736-5739. Thus, this one step strategy should be used, since it is highly preferable to reach high yields at the start of synthesis and that it is well known that it is very exceptional that the yield in three steps is better than in one step. According to the invention, this 3 steps synthesis of compound III or 3, reaches better yields than the one step.

According to a second aspect, the present invention relates to the preparation of the specific product 11, named 6-azido-2,4-diacetamido-2,4,6-trideoxy-D-mannose 11, here-below:

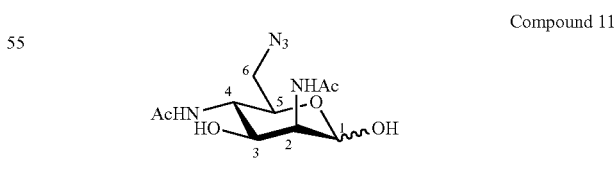

Compound 11 from commercially available D-galactose pentaacetate or D-galactose tetraacetate or tetraacetyl D-galactosyl trichloroacetimidate, according to the following reaction steps. It is apparent that chemical reaction scheme I or scheme 1, here-below, forms an integral part of the invention and is claimed in all its aspects, in part or in combination.

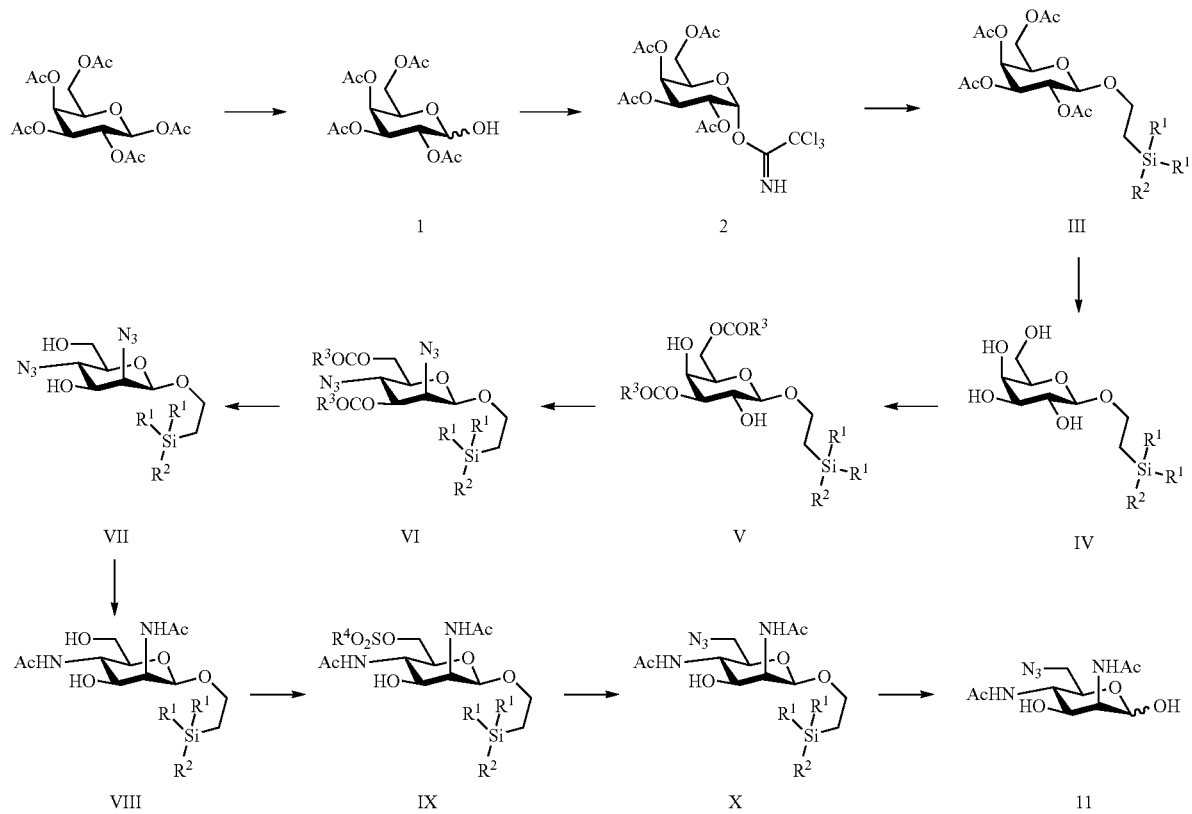

Wherein:

$R^1$ can be a $C_1$ to $C_6$ alkyl including methyl, ethyl, isopropyl; aryl including phenyl; each of these groups being substituted or not;

and $R^2$ can be a $C_1$ to $C_6$ alkyl including methyl, ethyl, isopropyl, tert-butyl, isobutyl; each of these groups being substituted or not;

and $R^3$ can be a $C_1$ to $C_6$ alkyl including methyl, ethyl, propyl, butyl, t-butyl; aryl including phenyl, para-methoxyphenyl; each of these groups being substituted or not;

and $R^4$ can be a $C_1$ to $C_6$ alkyl including methyl, ethyl, propyl; $C_1$ to $C_6$ perfluoroalkyl including trifluoromethyl, pentafluoroethyl; or aryl including para-methylphenyl, para-nitrophenyl; each of these groups being substituted or not;

The invention further relates to the following new synthesis intermediate compound, which is claimed as new compound:

Formula X

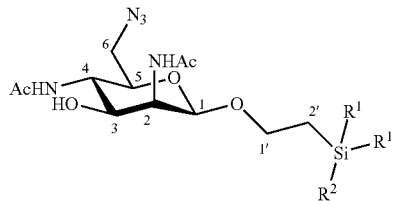

Wherein:

$R^1$ can be a $C_1$ to $C_6$ alkyl including methyl, ethyl, isopropyl; aryl including phenyl; each of these groups being substituted or not;

and $R^2$ can be a $C_1$ to $C_6$ alkyl including methyl, ethyl, isopropyl, tert-butyl, isobutyl; each of these groups being substituted or not;

More precisely, the invention relates to the specific synthesis intermediate compound 10, which is claimed as new compound, named 1'-trimethylsilylethanyl 6-azido-2,4-diacetamido-2,4,6-trideoxy-β-D-mannopyranoside 10, here-below:

Compound 10

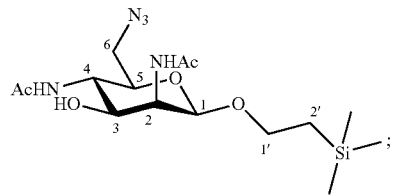

The invention further relates to the following new synthesis intermediate compound, which is claimed as new compound:

Formula IX

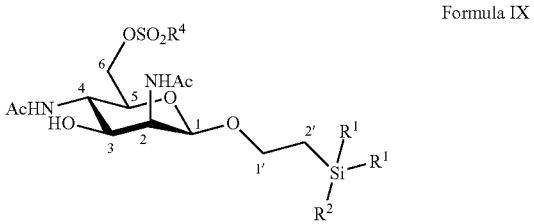

Wherein:

$R^1$ can be a $C_1$ to $C_6$ alkyl including methyl, ethyl, isopropyl; aryl including phenyl; each of these groups being substituted or not;

and $R^2$ can be a $C_1$ to $C_6$ alkyl including methyl, ethyl, isopropyl, tert-butyl, isobutyl; each of these groups being substituted or not;

and $R^4$ can be a $C_1$ to $C_6$ alkyl including methyl, ethyl, propyl; $C_1$ to $C_6$ perfluoroalkyl including trifluoromethyl, pentafluoroethyl; or aryl including para-methylphenyl, para-nitrophenyl; each of these groups being substituted or not;

More precisely, the invention relates to the specific synthesis intermediate compound 9, which is claimed as new compound, named 1'-trimethylsilylethanyl 2,4-diacetamido-2,4-dideoxy-6-O-mesyl-β-D-mannopyranoside 9, here-below:

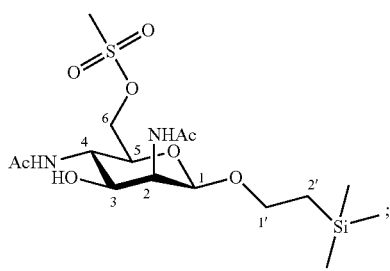

Compound 9

The invention further relates to the following new synthesis intermediate compound, which is claimed as new compound:

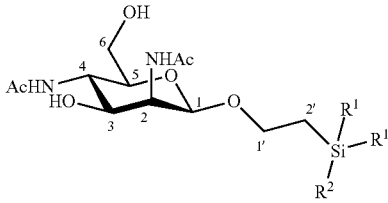

Formula VIII

Wherein
$R^1$ can be a $C_1$ to $C_6$ alkyl including methyl, ethyl, isopropyl; aryl including phenyl; each of these groups being substituted or not;

and $R^2$ can be a $C_1$ to $C_6$ alkyl including methyl, ethyl, isopropyl, tert-butyl, isobutyl; each of these groups being substituted or not;

More precisely, the invention relates to the specific synthesis intermediate compound 8, which is claimed as new compound, named 1'-trimethylsilylethanyl 2,4-diacetamido-2,4-dideoxy-β-D-mannopyranoside 8, here-below:

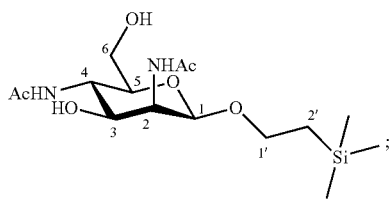

Compound 8

The invention further relates to the following new synthesis intermediate compound, which is claimed as new compound:

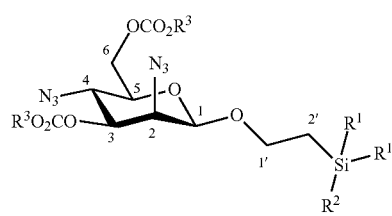

Formula VI

Wherein:
$R^1$ can be a $C_1$ to $C_6$ alkyl including methyl, ethyl, isopropyl; aryl including phenyl; each of these groups being substituted or not;

and $R^2$ can be a $C_1$ to $C_6$ alkyl including methyl, ethyl, isopropyl, tert-butyl, isobutyl; each of these groups being substituted or not;

and $R^3$ can be a $C_1$ to $C_6$ alkyl including methyl, ethyl, propyl, butyl, t-butyl; aryl including phenyl, para-methoxyphenyl; each of these groups being substituted or not;

More precisely, the invention relates to the new specific synthesis intermediate compound 6, which is claimed as new compound, named 1'-trimethylsilylethanyl 2,4-diazido-2,4-dideoxy-3,6-di-O-benzoyl-β-D-mannopyranoside 6, here-below:

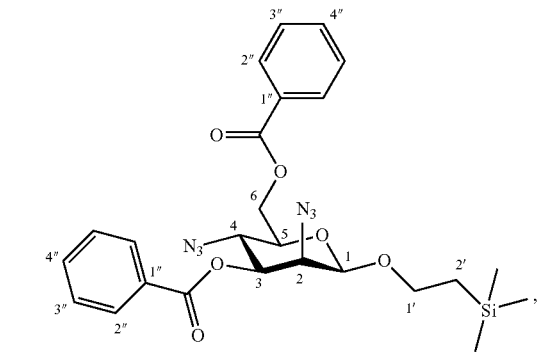

Compound 6

The invention further relates to the following new synthesis intermediate compound, which is claimed as new compound:

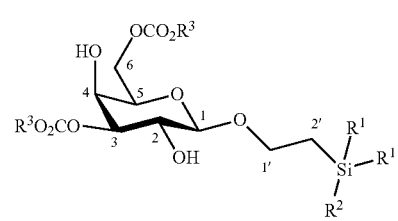

Formula V

Wherein:
$R^1$ can be a $C_1$ to $C_6$ alkyl including methyl, ethyl, isopropyl; aryl including phenyl; each of these groups being substituted or not;

and $R^2$ can be a $C_1$ to $C_6$ alkyl including methyl, ethyl, isopropyl, tert-butyl, isobutyl; each of these groups being substituted or not;

and $R^3$ can be a $C_1$ to $C_6$ alkyl including methyl, ethyl, propyl, butyl, t-butyl; aryl including phenyl, para-methoxyphenyl; each of these groups being substituted or not;

More precisely, the invention relates to the specific new synthesis intermediate compound 5, which is claimed as new compound, named 1'-trimethylsilylethanyl 3,6-di-O-benzoyl-β-D-galactopyranoside 5, here-below:

Compound 5

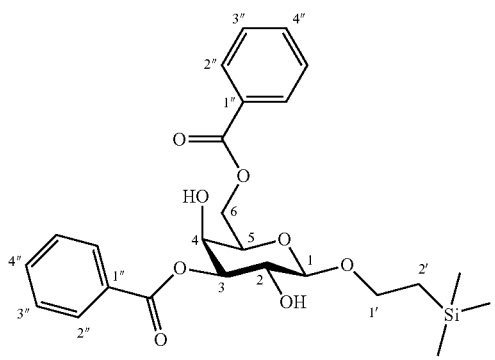

According to the present invention, all the percentages are given by mole, the temperature is in °C., the pressure is atmospheric pressure, unless otherwise stated.

DETAILED DESCRIPTION OF THE BEST EMBODIMENT

According to the invention, and in reference to Scheme 1 here-below, the target compound, 6-azido-2,4-diacetamido-2,4,6-trideoxy-D-mannose 11, was prepared in 13 steps from commercially available β-D-galactose pentaacetate with an overall yield of 8 mol % and with a high purity of more than 95% by NMR analysis involving simple purification steps.

According to specific embodiments the selective deprotection of the hydroxyl group at the anomeric position of β-D-galactose pentaacetate with ethylenediamine in the presence of glacial acetic acid in dichloromethane gave compound 1 in a good 90% yield [1]. Activation of this hydroxyl group with trichloroacetonitrile in the presence of 1,8-diazabicyclo(5.4.0)undec-7-ene in dichloromethane gave trichloroacetimidate 2 with 72% yield [2]. This glycosyl donor 2 was confirmed by $^1$H NMR to be the thermodynamically favored alpha anomer. Glycosylation of trimethylsilylethanol with compound 2 in the presence of trimethylsilyl trifluoromethanesulfonate in dry dichloromethane at −35° C. gave compound 3 in a good 76% yield [3]. Deacetylation using potassium carbonate [4] and selective benzoylation using the method developed by Lee and Taylor led to compound 5 (70% yield over 2 steps) [5]. Conversion of compound 5 into the bis-triflate derivative, and its subsequent reaction with tetra-n-butylammonium azide in toluene resulted into the bis-azido compound 6 (83% yield over 2 steps) [6], the manno configuration of which was confirmed by $^1$H NMR spectroscopy ($J_{1,2}$=1.1 Hz; $J_{2,3}$=3.6 Hz; $J_{3,4}$=10.2 Hz; $J_{4,5}$=10.0 Hz). Debenzoylation of (6) in the presence of potassium carbonate and reduction of the azido groups with palladium hydroxide on charcoal in an hydrogen atmosphere was followed by N-acetylation to give compound 8 in a good yield (66% over 3 steps) [6]. The azido derivative 10 was obtained with a lower yield (36% over 2 steps) by selective mesylation in pyridine, with subsequent nucleophilic substitution using sodium azide in N,N-dimethylformamide [7]. The final product 11 was obtained in a good yield (84%) from compound 10 by deprotection of the anomeric position using trifluoroacetic acid in dichloromethane [8].

Purification of product 11 is performed easily over inverse phase C18 silica. The purity of the final product is more than 95% by NMR analysis, and the overall yield for the synthesis of the product 11 is 8 mol %.

EXAMPLES OF SYNTHESIS OF THE INVENTION

Materials and Methods:

Thin layer chromatography was performed over Merck 60 F254 with detection by UV, and/or by charring with sulphuric acid or KMnO$_4$ or phosphomolybdic acid solutions. Silica gel 60 40-63 μm was used for flash column chromatography.

NMR spectra were taken on Bruker Avance 300 or 500 MHz spectrometers, using the residual protonated solvent as internal standard. Chemical shifts δ are given in parts per million (ppm) and coupling constants are reported as Hertz (Hz). Splitting patterns are designated as singlet (s), doublet (d), triplet (t), doublet of doublet (dd), doublet of doublet of doublet (ddd). Splitting patterns that could not be interpreted or easily visualized are designated as multiplet (m).

Mass spectra were taken on a Waters LCT Premier XE (ToF), with electrospray ionization in the positive (ESI$^+$) mode of detection.

IR-FT spectra were recorded on a Perkin Elmer Spectrum 100 spectrometer. Characteristic absorptions are reported in cm$^{-1}$.

Specific optical rotations were measured at 20° C. with an Anton Paar MCP 300 polarimeter in a 10-cm cell at 20° C. and 589 nm.

All chemical reagents were of analytical grade, obtained from commercial sources, and used without further purifications.

Invention Example 1

Synthesis of 6-azido-2,4-diacetamido-2,4,6-trideoxy-D-mannose (11) (Man2NAc4NAc6N$_3$)

Compound 11

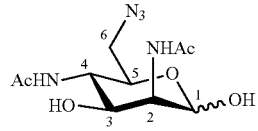

To a solution of compound 10 (77.0 mg, 0.20 mmol, 1.0 eq.) in CH$_2$Cl$_2$ (4.0 mL, 0.05 M) was added trifluoroacetic acid (1.5 mL, 2.3 g, 20.0 mmol, 100.0 eq.) at room temperature under an argon atmosphere. The reaction mixture was stirred at room temperature for 3 hours. The reaction mixture was diluted with toluene and ethyl acetate, then solvent were evaporated until dryness. Two others co-evaporations with toluene and ethyl acetate gave the crude solid. The residue was purified with C18 cartridge with H$_2$O elution. Lyophilisation gave compound 11 (47.9 mg, 84%) as a white powder. Purity of more than 95% by NMR analysis.

Rf (CH$_2$Cl$_2$/CH$_3$OH 88:12): 0.23.

IR (cm$^{-1}$): 3302, 2988, 2107, 1646, 1552, 1376, 1075.

HMRS (ESI$^+$): [M+H]$^+$ (C$_{10}$H$_{18}$N$_5$O$_5^+$) Calc. m/z: 288.1302, found: 288.1297.

Compound 11β:

$^1$H-NMR (exchange with D$_2$O) (500 MHz, CD$_3$OD) δ: 5.09 (d, 1H, J$_{1,2}$ 1.6 Hz, H-1); 4.25 (dd, 1H, J$_{2,3}$ 4.6, J$_{1,2}$ 1.6 Hz, H-2); 4.06 (dd, 1H, J$_{3,4}$ 10.1, J$_{2,3}$ 4.6 Hz, H-3); 3.96 (ddd, 1H, J$_{4,5}$ 10.4, J$_{5,6a}$ 7.0, J$_{5,6b}$ 2.1 Hz, H-5); 3.93 (dd, 1H, J$_{4,5}$ 10.4, J$_{3,4}$ 10.1 Hz, H-4); 3.40 (dd, 1H, J$_{6a,6b}$ 13.3, J$_{5,6a}$ 7.0 Hz, H-6a); 3.27 (dd, 1H, J$_{6a,6b}$ 13.3, J$_{5,6b}$ 2.1 Hz, H-6b); 2.04 (s, 3H, COCH$_3$); 1.98 (s, 3H, COCH$_3$).

$^{13}$C-NMR (125 MHz, CD$_3$OD) δ: 174.5, 174.3 (2 C=O); 94.6 (C-1); 71.9 (C-5); 68.0 (C-3); 54.9 (C-2); 53.5 (C-6); 51.3 (C-4); 22.9 (COCH$_3$); 22.7 (COCH$_3$).

Compound 11α:

$^1$H-NMR (exchange with D$_2$O) (500 MHz, CD$_3$OD) δ: 4.84 (d, 1H, J$_{1,2}$ 1.6 Hz, H-1); 4.44 (dd, 1H, J$_{2,3}$ 4.1, J$_{1,2}$ 1.6 Hz, H-2); 3.79 (dd, 1H, J$_{4,5}$ 10.6, J$_{3,4}$ 9.8 Hz, H-4); 3.73 (dd, 1H, J$_{3,4}$ 10.6, J$_{3,2}$ 4.1 Hz, H-3); 3.48 (dd, 1H, J$_{6a,6b}$ 12.8, J$_{6a,5}$ 8.0 Hz, H-6a); 3.41 (ddd, 1H, J$_{4,5}$ 9.8, J$_{5,6a}$ 8.0, J$_{5,6b}$ 2.0 Hz, H-5); 3.28 (dd, 1H, J$_{6a,6b}$ 12.8, J$_{6b,5}$ 2.0 Hz, H-6b); 2.08 (s, 3H, COCH$_3$); 1.98 (s, 3H, COCH$_3$).

$^{13}$C-NMR (125 MHz, CD$_3$OD) δ: 174.5, 174.3 (2 C=O); 95.1 (C-1); 76.7 (C-5); 72.0 (C-3); 55.5 (C-2); 53.4 (C-6); 51.3 (C-4); 23.0 (COCH$_3$); 22.7 (COCH$_3$).

Invention Example 2

Synthesis of 1'-trimethylsilylethanyl 6-azido-2,4-diacetamido-2,4,6-trideoxy-β-D-mannopyranoside (10)

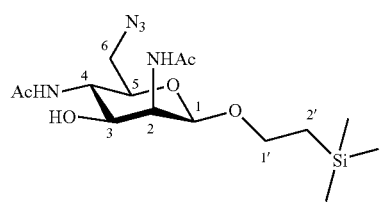

Compound 10

The compound 9 (154.9 mg, 0.35 mmol, 1.0 eq.) and sodium azide (91.4 mg, 1.40 mmol, 4.0 eq.) were dissolved in dry dimethylformamide (7.0 mL, 0.05 M). The reaction mixture was stirred for 15 h at 80° C. Then the reaction mixture was cooled to room temperature and the solvent was evaporated under reduced pressure. The residue was purified by flash column chromatography over silica gel (CH$_2$Cl$_2$/CH$_3$OH 100:0 to 90:10) to give compound 10 (77.4 mg, 57%) as colourless oil. Purity of more than 95% by NMR analysis.

Rf (CH$_2$Cl$_2$/CH$_3$OH 9:1): 0.26.

IR (cm$^{-1}$): 3278, 2097, 1657, 1551, 1068.

$^1$H-NMR (500 MHz, CDCl$_3$) δ: 6.26 (br d, 1H, J$_{4,NH}$ 5.8 Hz, NH-(4)); 6.08 (d, 1H, J$_{2,NH}$ 5.2 Hz, NH-(2)); 5.54-5.36 (br s, 1H, OH-(3)); 4.66 (d, 1H, J$_{1,2}$ 1.5 Hz, H-1); 4.31 (ddd, 1H, J$_{2,NH}$ 5.2, J$_{2,3}$ 2.6, J$_{1,2}$ 1.5 Hz, H-2); 4.00 (ddd, 1H, J$_{1'a,2'}$ 9.9, J$_{1'a,1'b}$ 9.2, J$_{1'a,2'}$ 7.0 Hz, H-1'a); 3.80-3.71 (m, 2H, H-3, H-4); 3.62 (ddd, 1H, J$_{1'b,2'}$ 9.8, J$_{1'a,1'b}$ 9.2, J$_{1'b,2'}$ 6.7 Hz, H-1'b); 3.47 (dd, 1H, J$_{6a,6b}$ 13.0, J$_{5,6a}$ 8.3 Hz, H-6a); 3.42 (ddd, 1H, J$_{4,5}$ 9.1, J$_{5,6a}$ 8.3, J$_{5,6b}$ 1.3 Hz, H-5); 3.19 (dd, 1H, J$_{6a,6b}$ 13.0, J$_{5,6b}$ 1.3 Hz, H-6b); 2.08 (s, 3H, COCH$_3$ (2)); 1.94 (s, 3H, COCH$_3$ (4)); 0.96 (ddd, 1H, J$_{2'a,2b'}$ 13.8, J$_{2'a,1'a}$ 9.9, J$_{2'a,1'b}$ 6.7 Hz, H-2'a); 0.92 (ddd, 1H, J$_{2'a,2b'}$ 13.8, J$_{2'b,1'b}$ 9.8, J$_{2'b,1'a}$ 7.0 Hz, H-2'b); 0.00 (s, 9H, Si(CH$_3$)$_3$).

$^{13}$C-NMR (125 MHz, CDCl$_3$) δ: 174.6 (C=O (2)); 172.0 (C=O (4)); 98.2 (C-1); 77.5 (C-5); 72.5 (C-3); 67.5 (C-1'); 55.7 (C-2); 52.3 (C-6); 50.8 (C-4); 23.5 (COCH$_3$); 23.4 (COCH$_3$); 18.1 (C-2'); −1.1 (Si(CH$_3$)$_3$).

HMRS (ESI$^+$): [2M+Na]$^+$ (C$_{30}$H$_{58}$N$_{10}$O$_{10}$Si$_2$Na$^+$) Calc. 797.3768, found 797.3795.

[α]$_D$=−282.0 (c 1.0, CHCl$_3$).

Invention Example 3

Synthesis of 1'-trimethylsilylethanyl 2,4-diacetamido-2,4-dideoxy-6-O-mesyl-β-D-mannopyranoside (9)

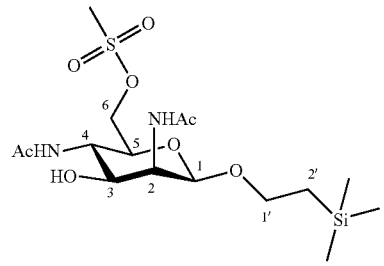

Compound 9

To a solution of compound 8 (59.8 mg, 0.16 mmol, 1.0 eq.) in dry pyridine (1.5 mL, 0.10 M) at −10° C. was added mesyl chloride (19.1 μL, 28.3 mg, 0.25 mmol, 1.5 eq.). The reaction mixture was stirred at −10° C. for 1 hour, then mesyl chloride (19.1 μL, 28.3 mg, 0.25 mmol, 1.5 eq.) was added and the reaction mixture was stirred at −10° C. for 30 min, until complete conversion. The reaction mixture was then quenched with CH$_3$OH and solvent evaporated under vacuum. The crude residue was purified by flash column chromatography over silica gel (CH$_2$Cl$_2$/CH$_3$OH 100:0 to 90:10) to give compound 9 (44.2 mg, 63%) as white powder. Purity of more than 95% by NMR analysis.

Rf (CH$_2$Cl$_2$/CH$_3$OH 9:1): 0.38.

$^1$H-NMR (500 MHz, CDCl$_3$) δ: 6.67 (d, 1H, J$_{4,NH}$ 7.8 Hz, NH-(4)); 6.33 (d, 1H, J$_{2,NH}$ 6.3 Hz, NH-(2)); 5.44-5.20 (br s, 1H, OH-(3)); 4.63 (d, 1H, J$_{1,2}$ 1.6 Hz, H-1); 4.36 (dd, 1H, J$_{6a,6b}$ 11.6, J$_{5,6a}$ 2.3 Hz, H-6a); 4.34 (ddd, 1H, J$_{2,NH}$ 6.3, J$_{2,3}$ 3.1, J$_{1,2}$ 1.6 Hz, H-2); 4.30 (dd, 1H, J$_{6a,6b}$ 11.6, J$_{5,6b}$ 6.1 Hz, H-6b); 3.94 (ddd, 1H, J$_{1'a,2'}$ 9.9, J$_{1'a,1'b}$ 8.9, J$_{1'a,2'}$ 7.2 Hz, H-1'a); 3.85 (dd, 1H, J$_{3,4}$ 10.4, J$_{2,3}$ 3.1 Hz, H-3); 3.78 (ddd, 1H, J$_{4,5}$ 10.1, J$_{3,4}$ 10.4, J$_{4,NH}$ 7.8 Hz, H-4); 3.61 (ddd, 1H, J$_{1'b,2'}$ 9.6, J$_{1'a,1'b}$ 8.9, J$_{1'b,2'}$ 7.3 Hz, H-1'b); 3.58 (ddd, 1H, J$_{4,5}$ 10.1, J$_{5,6b}$ 6.1, J$_{5,6a}$ 2.3 Hz, H-5); 3.03 (s, 3H, SCH$_3$); 2.05 (s, 3H, COCH$_3$); 1.95 (s, 3H, COCH$_3$); 0.97-0.86 (m, 2H, 2H-2'); −0.01 (s, 9H, Si(CH$_3$)$_3$).

$^{13}$C-NMR (125 MHz, CDCl$_3$) δ: 174.3, 172.3 (2 C=O); 98.2 (C-1); 74.4 (C-5); 72.0 (C-3); 69.8 (C-6); 67.5 (C-1'); 55.0 (C-2); 49.6 (C-4); 38.0 (SCH$_3$); 23.5 (COCH$_3$-(4)); 23.4 (COCH$_3$-(2)); 18.1 (C-2'); −1.1 (Si(CH$_3$)$_3$).

HMRS (ESI$^+$): [2M+H]$^+$ (C$_{32}$H$_{65}$N$_4$O$_{16}$Si$_2$S$_2^+$) Calc. 881.3370, found 881.3410.

Invention Example 4

Synthesis of 1'-trimethylsilylethanyl 2,4-diacetamido-2,4-dideoxy-β-D-mannopyranoside (8)

Compound 8

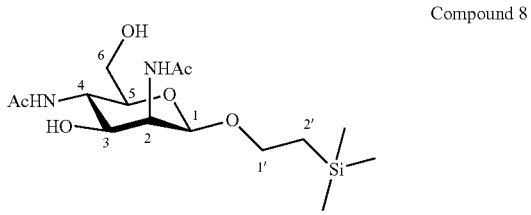

A solution of compound 7 (237.8 mg, 0.72 mmol, 1.0 eq.) in $CH_3OH$ (7.2 mL, 0.10 M) was hydrogenated with 20% $Pd(OH)_2/C$ (101.2 mg, 0.14 mmol, 0.20 eq.) at 40° C. for 3 hours under an hydrogen atmosphere. The catalyst was filtered off through Celite® plug and the filtrate was concentrated to dryness. The crude residue was dissolved in $CH_3OH$ (7.2 mL, 0.10 M), acetic anhydride (0.27 mL, 293.8 mg, 2.88 mmol, 4.0 eq.) was added and the mixture was stirred for 1 hour at room temperature. The reaction mixture was concentrated until dryness. The residue was purified by flash column chromatography over silica gel ($CH_2Cl_2/CH_3OH$, 100:0 to 90:10) to give compound 8 (181.3 mg, 69%) as a white powder. Purity of more than 95% by NMR analysis.

Rf ($CH_2Cl_2/CH_3OH$ 9:1): 0.34.

IR ($cm^{-1}$): 3676, 2988, 2902, 1407, 1382, 1250, 1230, 1066, 1028.

$^1$H-NMR (exchange with $D_2O$) (500 MHz, $CD_3OD$) δ: 4.58 (d, 1H, $J_{1,2}$ 1.4 Hz, H-1); 4.45 (dd, 1H, $J_{2,3}$ 3.8, $J_{1,2}$ 1.4 Hz, H-2); 3.99 (ddd, 1H, $J_{1'a,2'a}$ 9.5, $J_{1'a,1'b}$ 8.4, $J_{1'a,2'b}$ 7.3 Hz, H-1'a); 3.79 (dd, 1H, $J_{4,5}$ 10.4, $J_{3,4}$ 10.1 Hz, H-4); 3.76 (dd, 1H, $J_{3,4}$ 10.1, $J_{2,3}$ 3.8 Hz, H-3); 3.68 (dd, 1H, $J_{6a,6b}$ 12.5, $J_{5,6a}$ 2.3 Hz, H-6a); 3.64 (dd, 1H, $J_{6a,6b}$ 12.5, $J_{5,6b}$ 3.9 Hz, H-6b); 3.63 (ddd, 1H, $J_{1'b,2'b}$ 9.3, $J_{1'a,1'b}$ 8.4, $J_{1'b,2'a}$ 6.9 Hz, H-1'b); 3.24 (dd, 1H, $J_{4,5}$ 10.1, $J_{5,6b}$ 3.9, $J_{5,6a}$ 2.3 Hz, H-5); 2.03 (s, 3H, $COCH_3$); 1.99 (s, 3H, $COCH_3$); 0.93 (ddd, 1H, $J_{2'a,2'b}$ 15.0, $J_{2'a,1'a}$ 9.5, $J_{2'a,1'b}$ 6.9 Hz, H-2'a); 0.90 (ddd, 1H, $J_{2'a,2'b}$ 15.0, $J_{2'b,1'b}$ 9.3, $J_{2'b,1'a}$ 7.3 Hz, H-2'b); 0.02 (s, 9H, $Si(CH_3)_3$).

$^{13}$C-NMR (125 MHz, $CD_3OD$) δ: 174.9, 174.8 (2 C=O); 100.6 (C-1); 77.6 (C-5); 72.2 (C-3); 67.9 (C-1'); 62.6 (C-6); 54.8 (C-2); 50.1 (C-4); 22.9 ($COCH_3$); 22.8 ($COCH_3$); 18.9 (C-2'); −1.1 ($Si(CH_3)_3$).

HRMS ($ESI^+$): $[M+H]^+$ ($C_{15}H_{31}N_2O_6Si^+$) Calc. 363.1946, found 363.1959.

$[α]_D$=−45.2 (c 1.0, $CH_3OH$).

Invention Example 5

Synthesis of 1'-trimethylsilylethanyl 2,4-diazido-2,4-dideoxy-β-D-mannopyranoside (7), Known from WO 2015/063173

Compound 7

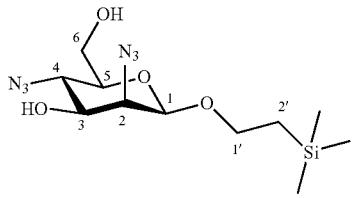

To a solution of compound 6 (1.58 g, 2.94 mmol, 1.0 eq.) in $CH_3OH$ (30.0 mL, 0.10 M), was added $K_2CO_3$ (0.06 g, 0.44 mmol, 0.15 eq.) under an argon atmosphere. The reaction mixture was stirred at room temperature for 16 hours. Dowex® $H^+$ resin was added to the reaction mixture until neutral pH. The suspension was filtered off, washed with $CH_3OH$, then the filtrate was concentrated. The residue was purified by flash column chromatography over silica gel (Heptane/Ethyl Acetate, 100:0 to 60:40) to give compound 7 (0.93 g, 96%) as a colourless oil. Purity of more than 95% by NMR analysis.

Rf (Cyclohexane/Ethyl Acetate 6:4): 0.59.

IR ($cm^{-1}$): 2112 ($N_3$), 1250, 1073, 1028, 861, 838.

$^1$H-NMR (exchange with $D_2O$) (500 MHz, $CD_3OD$) δ: 4.65 (d, 1H, $J_{1,2}$ 0.9 Hz, H-1); 4.02 (ddd, 1H, $J_{1'a,2'a}$ 10.2, $J_{1'a,1'b}$ 9.7, $J_{1'a,2'b}$ 6.1 Hz, H-1'a); 3.84 (dd, 1H, $J_{2,3}$ 3.7, $J_{1,2}$ 0.9 Hz, H-2); 3.80 (dd, 1H, $J_{6a,6b}$ 12.2, $J_{5,6a}$ 2.1 Hz, H-6a); 3.77 (dd, 1H, $J_{3,4}$ 9.8, $J_{2,3}$ 3.7 Hz, H-3); 3.69 (dd, 1H, $J_{6a,6b}$ 12.2, $J_{5,6b}$ 5.0 Hz, H-6b); 3.64 (ddd, 1H, $J_{1'b,2'b}$ 10.0, $J_{1'a,1'b}$ 9.7, $J_{1'b,2'a}$ 6.4 Hz, H-1'b); 3.50 (dd, 1H, $J_{4,5}$ 10.2, $J_{3,4}$ 9.8 Hz, H-4); 3.11 (ddd, 1H, $J_{4,5}$ 10.2, $J_{5,6b}$ 5.0, $J_{5,6a}$ 2.1 Hz, H-5); 1.00 (ddd, 1H, $J_{2'a,2'b}$ 13.9, $J_{2'a,1'a}$ 10.2, $J_{2'a,1'b}$ 6.4 Hz, H-2'a); 0.95 (ddd, 1H, $J_{2'a,2'b}$ 13.9, $J_{2'b,1'b}$ 10.0, $J_{2'b,1'a}$ 6.1 Hz, H-2'b); 0.04 (s, 9H, $Si(CH_3)_3$).

$^{13}$C-NMR (125 MHz, $CD_3OD$) δ: 100.8 (C-1); 76.9 (C-5); 73.8 (C-3); 68.2 (C-1'); 66.8 (C-2); 62.7 (C-6); 60.9 (C-4); 19.1 (C-2'); −1.2 ($Si(CH_3)_3$).

HRMS ($ESI^+$): $[2M+H]^+$ ($C_{22}H_{45}N_{12}O_8Si_2^+$) Calc. 661.3016, found 661.3021.

$[α]_D$=−72.8 (c 1.0, $CH_3OH$).

Invention Example 6

Synthesis of 1'-trimethylsilylethanyl 2,4-diazido-2,4-dideoxy-3,6-di-O-benzoyl-β-D-mannopyranoside (6)

Compound 6

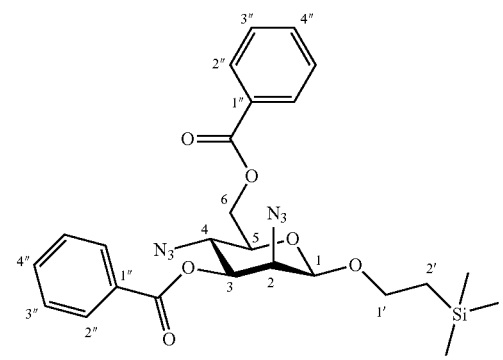

Trifluoromethanesulfonic anhydride (1.45 mL, 2.44 g, 8.6 mmol, 3.0 eq.) was added dropwise at 0° C. to a solution of compound 5 (1.41 g, 2.88 mmol, 1.0 eq.) and dry pyridine (1.40 mL, 1.37 g, 17.3 mmol, 6.0 eq.) in $CH_2Cl_2$ (20.0 mL, 0.15 M). The reaction mixture was stirred at 0° C. for 1 h30, diluted with $CH_2Cl_2$, and washed successively with $H_2O$, a solution of 1N aq. HCl, a saturated solution of NaCl and then concentrated under vacuum. The crude bis-triflate obtained was dissolved in toluene (20.0 mL, 0.15 M) and tetra-n-butylammonium azide (4.92 g, 17.3 mmol, 6.0 eq.) was added. After stirring 1 h30 at 70° C. and 1 h30 at 100° C., the mixture was cooled, diluted with toluene, washed twice with water, a saturated solution of NaCl, and concentrated under vaccum. The residue was purified by flash column chromatography over silica gel (Petroleum Ether/Ethyl Acetate 100:0 to 80:20) to give compound 6 (1.28 g, 83%) as a colourless oil. Purity of more than 95% by NMR analysis.

Rf (Cyclohexane/Ethyl Acetate 6:4): 0.82.

IR (cm$^{-1}$): 2112 (N$_3$), 1724, 1268, 1094, 710.

$^1$H-NMR (500 MHz, CDCl$_3$) δ: 8.11 (dd, 2H, $^3$J 8.3, $^4$J 1.1 Hz, 2H-2"a); 8.08 (dd, 2H, $^3$J 8.3, $^4$J 1.1 Hz, 2H-2"b); 7.61 (tt, 1H, $^3$J 7.4, $^4$J 1.1 Hz, H-4"a); 7.57 (tt, 1H, $^3$J 7.4, $^4$J 1.1 Hz, H-4"b); 7.48 (dd, 2H, $^3$J 8.3, $^3$J 7.4 Hz, 2H-3"a); 7.45 (dd, 2H, $^3$J 8.3, $^3$J 7.4 Hz, 2H-3"b); 5.13 (dd, 1H, J$_{3,4}$ 10.2, J$_{2,3}$ 3.6 Hz, H-3); 4.73 (d, 1H, J$_{1,2}$ 1.1 Hz, H-1); 4.70 (dd, 1H, J$_{6a,6b}$ 12.0, J$_{5,6a}$ 2.4 Hz, H-6a); 4.54 (dd, 1H, J$_{6a,6b}$ 12.0, J$_{5,6b}$ 5.6 Hz, H-6b); 4.25 (dd, 1H, J$_{2,3}$ 3.6, J$_{1,2}$ 1.1 Hz, H-2); 4.01 (dd, 1H, J$_{3,4}$ 10.2, J$_{4,5}$ 10.0 Hz, H-4); 4.03-3.96 (m, 1H, H-1'a); 3.66-3.58 (m, 1H, H-1'b); 3.57 (ddd, 1H, J$_{4,5}$ 10.0, J$_{5,6b}$ 5.6, J$_{5,6a}$ 2.4 Hz, H-5); 1.04-0.92 (m, 2H, 2H-2'); −0.01 (s, 9H, Si(CH$_3$)$_3$).

$^{13}$C-NMR (125 MHz, CDCl$_3$) δ: 166.4, 165.8 (2 C=O); 134.1, 133.5 (2 C-4"); 130.3, 130.0 (4 C-2"); 129.9 (C-1"); 128.9 (2 C-3"); 128.8 (C-1"); 128.7 (2 C-3"); 99.3 (C-1); 74.5 (C-3); 73.0 (C-5); 67.9 (C-1'); 64.0 (C-6); 61.8 (C-2); 57.8 (C-4); 18.3 (C-2'); −1.2 (Si(CH$_3$)$_3$).

HRMS (ESI$^+$): [M+Na]$^+$ (C$_{25}$H$_{30}$N$_6$O$_6$NaSi$^+$) Calc. 561.1888, found 561.1895.

[α]$_D$=−50.6 (c 1.0, CHCl$_3$).

Invention Example 7

Synthesis of 1'-trimethylsilylethanyl 3,6-di-O-benzoyl-β-D-galactopyranoside (5)

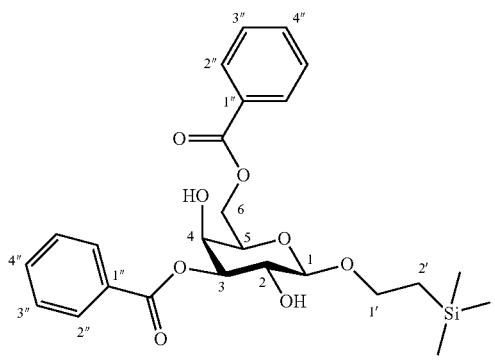

Compound 5

To a solution of compound 4 (1.17 g, 4.17 mmol, 1.0 eq.) and 2-aminoethyl diphenylborinate (95.0 mg, 0.42 mmol, 0.10 eq.) in dry CH$_3$CN (21.0 mL, 0.20 M) were added successively N,N-diisopropylethylamine (2.91 mL, 16.7 mmol, 4.0 eq.) and benzoyl chloride (1.93 mL, 16.7 mmol, 4.0 eq.) at 0° C. under an argon atmosphere. The resulting mixture was stirred at 0° C. for 30 minutes then was allowed to warm up at room temperature and stirred for 1 hour. The mixture was then diluted with ethyl acetate, washed with H$_2$O (30.0 mL), and extracted three times with ethyl acetate. The combined organic layers were washed with Brine, then dried over anhydrous Na$_2$SO$_4$, filtered, and concentrated under reduced pressure. The resulting crude material was purified by flash column chromatography over silica gel (Cyclohexane/Ethyl Acetate 90:10 to 70:30) to afford compound 5 (1.54 g, 75%) as a colourless foam. Purity of more than 95% by NMR analysis.

Rf (Cyclohexane/Ethyl Acetate 6:4): 0.47.

IR (cm$^{-1}$): 1718, 1277, 1117, 1071, 712.

$^1$H-NMR (exchange with D$_2$O) (300 MHz, CD$_3$OD) δ: 8.16-8.02 (m, 4H, 4H-2"); 7.65-7.57 (m, 2H, 2H-4"); 7.52-7.43 (m, 4H, 4H-3"); 5.03 (dd, 1H, J$_{2,3}$ 10.1, J$_{3,4}$ 3.5 Hz, H-3); 4.62 (dd, 1H, J$_{6a,6b}$ 11.3, J$_{5,6a}$ 7.8 Hz, H-6a); 4.47 (dd, 1H, J$_{6a,6b}$ 11.3, J$_{5,6b}$ 4.8 Hz, H-6b); 4.46 (d, 1H, J$_{1,2}$ 7.8 Hz, H-1); 4.23 (dd, 1H, J$_{3,4}$ 3.5, J$_{4,5}$ 1.0 Hz, H-4); 4.06 (ddd, 1H, J$_{5,6a}$ 7.8, J$_{5,6b}$ 4.8, J$_{4,5}$ 1.0 Hz, H-5); 3.98 (ddd, 1H, J$_{1'a,2'a}$ 11.3, J$_{1'a,1'b}$ 9.7, J$_{1'a,2'b}$ 6.1 Hz, H-1'a); 3.93 (dd, 1H, J$_{2,3}$ 10.1, J$_{1,2}$ 7.8 Hz, H-2); 3.69 (ddd, 1H, J$_{1'b,2'b}$ 11.1, J$_{1'a,1'b}$ 9.7, J$_{1'b,2'a}$ 6.1 Hz, H-1'b); 1.06 (ddd, 1H, J$_{2'a,2'b}$ 13.9, J$_{2'a,1'a}$ 11.3, J$_{2'a,1'b}$ 6.1 Hz, H-2'a); 0.98 (ddd, 1H, J$_{2'a,2'b}$ 13.9, J$_{2'b,1'b}$ 11.1, J$_{2'b,1'a}$ 6.1 Hz, H-2'b); −0.01 (s, 9H, Si(CH$_3$)$_3$).

$^{13}$C-NMR (125 MHz, CD$_3$OD) δ: 168.0, 167.9 (2 C=O); 134.5, 134.4 (2 C-4"); 131.7, 131.5 (2 C-1"); 131.0, 130.7 (4 C-2"); 129.8, 129.6 (4 C-3"); 104.5 (C-1); 78.1 (C-3); 74.0 (C-5); 70.2 (C-2); 68.3 (C-1'); 68.2 (C-4); 65.1 (C-6); 19.2 (C-2'); −1.3 (Si(CH$_3$)$_3$).

HRMS (ESI$^+$): [2M+Na]$^+$ (C$_{50}$H$_{64}$O$_{16}$NaSi$_2^+$) Calc. 999.3625, found 999.3680.

[α]$_D$=+31.6 (c 1.0, CH$_3$OH).

Invention Example 8

Synthesis of 1'-trimethylsilylethanyl β-D-galactopyranoside (4)

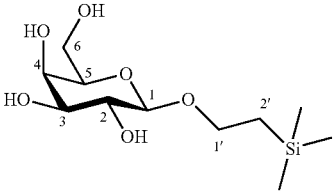

Compound 4

To a solution of compound 3 (2.15 g, 4.8 mmol, 1.0 eq.) in CH$_3$OH (25.0 mL, 0.20 M), was added K$_2$CO$_3$ (0.10 g, 0.7 mmol, 0.15 eq.) under an argon atmosphere. The reaction mixture was stirred at room temperature for 1 hour. Dowex® H$^+$ resin was added the reaction mixture until neutral pH. The suspension was filtered off, washed with CH$_3$OH, then the filtrate was concentrated to give compound 4 (1.25 g, 93%) as a white foam. Purity of more than 95% by NMR analysis.

Rf (CH$_2$Cl$_2$/CH$_3$OH 9:1): 0.17.

IR (cm$^{-1}$): 3380, 1250, 1059, 836.

$^1$H-NMR (exchange with D$_2$O) (300 MHz, CD$_3$OD) δ: 4.22 (d, 1H, J$_{1,2}$ 7.0 Hz, H-1); 4.01 (ddd, 1H, J$_{1'a,1'b}$ 11.5, J$_{1'a,1'b}$ 9.5, J$_{1'a,2'a}$ 5.9 Hz, H-1'a); 3.82 (dd, 1H, J$_{3,4}$ 3.0, J$_{4,5}$ 1.0 Hz, H-4); 3.76 (dd, 1H, J$_{6a,6b}$ 11.3, J$_{5,6a}$ 6.7 Hz, H-6a); 3.71 (dd, 1H, J$_{6a,6b}$ 11.3, J$_{5,6b}$ 5.5 Hz, H-6b); 3.62 (ddd, 1H, J$_{1'b,2'a}$ 11.3, J$_{1'a,1'b}$ 9.5, J$_{1'b,2'b}$ 6.0 Hz, H-1'b); 3.50 (dd, 1H, J$_{2,3}$ 9.4, J$_{1,2}$ 7.0 Hz, H-2); 3.49 (ddd, 1H, J$_{5,6a}$ 6.7, J$_{5,6b}$ 5.5, J$_{4,5}$ 1.0 Hz, H-5); 3.45 (dd, 1H, J$_{2,3}$ 9.4, J$_{3,4}$ 3.0 Hz, H-3); 1.06 (ddd, 1H, J$_{2'a,2'b}$ 13.8, J$_{2'a,1'b}$ 11.3, J$_{2'a,1'a}$ 5.9 Hz, H-2'a); 0.97 (ddd, 1H, J$_{2'a,2'b}$ 13.8, J$_{2'b,1'a}$ 11.5, J$_{2'b,1'b}$ 6.0 Hz, H-2'b); 0.03 (s, 9H, Si(CH$_3$)$_3$).

$^{13}$C-NMR (125 MHz, CD$_3$OD) δ: 104.6 (C-1); 76.8 (C-5); 75.3 (C-3); 72.7 (C-2); 70.5 (C-4); 68.2 (C-1'); 62.7 (C-6); 19.3 (C-2'); −1.3 (Si(CH$_3$)$_3$).

HRMS (ESI$^+$): [2M+Na]$^+$ (C$_{22}$H$_{48}$O$_{12}$NaSi$_2^+$) Calc. m/z: 583.2577, found: 583.2586.

[α]$_D$=−22.3 (c 1.0, CH$_3$OH).

Invention Example 9

Synthesis of 1'-trimethylsilylethanyl 2,3,4,6-tetra-O-acetyl-β-D-galactopyranoside (3)

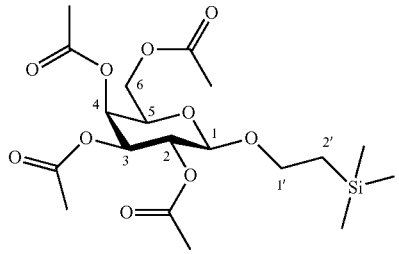

Compound 3

To a suspension of compound 2 (2.46 g, 5.0 mmol, 1.0 eq.) and trimethylsilylethanol (0.93 mL, 6.5 mmol, 1.3 eq.) in dry $CH_2Cl_2$ (50.0 mL, 0.10 M), was added TMSOTf (45 μL, 0.25 mmol, 0.05 eq.) at −35° C. under an argon atmosphere. The suspension was stirred at −35° C. for 30 min under an argon atmosphere. The reaction mixture was quenched by triethylamine (1.0 mL), then allowed to reach room temperature and concentrated under vacuum. The residue was purified by flash column chromatography over silica gel (Petroleum Ether/Ethyl Acetate 85:15 to 65:35) to afford compound 3 (1.70 g, 76%) as a colourless oil. Purity of more than 95% by NMR analysis.

Rf (Cyclohexane/Ethyl Acetate 6:4): 0.57.
IR ($cm^{-1}$): 1752, 1221, 772.
HRMS ($ESI^+$): $[M+Na]^+$ ($C_{19}H_{32}O_{10}NaSi^+$) Calc. m/z: 471.1657, found: 471.1677.
$^1$H-NMR (500 MHz, $CDCl_3$) δ: 5.36 (dd, 1H, $J_{3,4}$ 3.5, $J_{4,5}$ 1.1 Hz, H-4); 5.18 (dd, 1H, $J_{2,3}$ 10.4, $J_{1,2}$ 8.0 Hz, H-2); 4.99 (dd, 1H, $J_{2,3}$ 10.4, $J_{3,4}$ 3.5 Hz, H-3); 4.46 (d, 1H, $J_{1,2}$ 8.0 Hz, H-1); 4.18 (dd, 1H, $J_{6a,6b}$ 11.2, $J_{5,6a}$ 6.4 Hz, H-6a); 4.10 (dd, 1H, $J_{6a,6b}$ 11.2, $J_{5,6b}$ 7.1 Hz, H-6b); 3.97 (ddd, 1H, $J_{1'a,2'a}$ 10.9, $J_{1'a,1'b}$ 9.6, $J_{1'a,2'b}$ 5.3 Hz, H-1'a); 3.88 (ddd, 1H, $J_{5,6b}$ 7.1, $J_{5,6a}$ 6.4, $J_{4,5}$ 1.1 Hz, H-5); 3.55 (ddd, 1H, $J_{1'b,2'b}$ 10.4, $J_{1'a,1'b}$ 9.6, $J_{1'b,2'a}$ 6.7 Hz, H-1'b); 2.13, 2.03, 2.02, 1.96 (4s, 12H, $COCH_3$); 0.96 (ddd, 1H, $J_{2'a,2'b}$ 13.9, $J_{2'a,1'a}$ 10.9, $J_{2'a,1'b}$ 6.7 Hz, H-2'a); 0.89 (ddd, 1H, $J_{2'a,2'b}$ 13.9, $J_{2'b,1'b}$ 10.4, $J_{2'b,1'a}$ 5.3 Hz, H-2'b); −0.01 (s, 9H, $Si(CH_3)_3$).
$^{13}$C-NMR (125 MHz, $CDCl_3$) δ: 170.6, 170.5, 170.4, 169.6 (4 C=O); 101.0 (C-1); 71.3 (C-3); 70.8 (C-5); 69.2 (C-2); 67.8 (C-1'); 67.3 (C-4); 61.5 (C-6); 21.0, 20.9, 20.8 (4 $COCH_3$); 18.2 (C-2'); −1.2 ($Si(CH_3)_3$).
$[\alpha]_D$=−16.2 (c 1.0, $CHCl_3$).

Invention Example 10

Synthesis of O-(2,3,4,6-tetra-O-acetyl-β-D-galactopyranosyl)trichloroacetimidate (2)

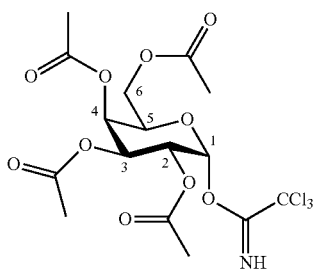

Compound 2

To a solution of compound 1 (6.42 g, 18.4 mmol, 1.0 eq.) in dry $CH_2Cl_2$ (90.0 mL, 0.20 M) was added trichloroacetonitrile (18.5 mL, 184.4 mmol, 10.0 eq.) and 1,8-diazabicyclo(5.4.0)undec-7-ene (0.55 mL, 3.7 mmol, 0.2 eq.). The reaction mixture was stirred at room temperature for 2 hours. The crude mixture was purified by flash column chromatography over silica gel (Petroleum Ether/Ethyl Acetate 90:10 to 50:50) to afford the compound 2 (6.53 g, 72%) as a white solid. Purity of more than 95% by NMR analysis.

Rf (Cyclohexane/Ethyl Acetate 6:4): 0.49.
IR ($cm^{-1}$): 1749, 1372, 1224, 1072.
$^1$H-NMR (500 MHz, $CDCl_3$) δ: 8.64 (s, 1H, NH); 6.58 (d, 1H, $J_{1,2}$ 3.5 Hz, H-1); 5.54 (dd, 1H, $J_{3,4}$ 3.2, $J_{4,5}$ 1.3 Hz, H-4); 5.41 (dd, 1H, $J_{2,3}$ 10.9, $J_{3,4}$ 3.2 Hz, H-3); 5.34 (dd, 1H, $J_{2,3}$ 10.9, $J_{1,2}$ 3.5 Hz, H-2); 4.42 (ddd, 1H, $J_{5,6b}$ 6.7, $J_{5,6a}$ 6.7, $J_{4,5}$ 1.3 Hz, H-5); 4.14 (dd, 1H, $J_{6a,6b}$ 11.3, $J_{5,6a}$ 6.7 Hz, H-6a); 4.06 (dd, 1H, $J_{6a,6b}$ 11.3, $J_{5,6b}$ 6.7 Hz, H-6b); 2.14, 2.00, 1.99, 1.99 (4s, 12H, $COCH_3$).
$^{13}$C-NMR (125 MHz, $CDCl_3$) δ: 170.5, 170.3, 170.3, 170.2 (4 C=O); 161.2 (CNH); 93.8 (C-1); 91.0 ($CCl_3$); 69.2 (C-5); 67.7 (C-3); 67.6 (C-4); 67.6 (C-2); 61.5 (C-6); 20.9, 20.8, 20.7 (4 $COCH_3$).
$[\alpha]_D$=+92.6 (c 1.0, $CHCl_3$).

Invention Example 11

Synthesis of 2,3,4,6-tetra-O-acetyl-D-galactopyranose (1)

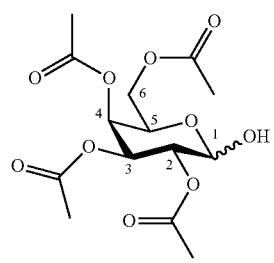

Compound 1

To a solution of ethylenediamine (2.24 mL, 2.02 g, 33.5 mmol, 1.1 eq.) in dry THF (61.0 mL, 0.50 M) was added dropwise glacial acetic acid (1.92 mL, 2.01 g, 33.5 mmol, 1.1 eq.) at 0° C. Then, commercially available 1,2,3,4,6-penta-O-acetyl-β-D-galactopyranoside (11.9 g, 30.5 mmol, 1.0 eq.) was added. The reaction mixture was stirred at room temperature under an argon atmosphere for 2 days. Then the reaction mixture was diluted with $CH_2Cl_2$ and the mixture was washed successively with HCl solution (1 N), saturated $NaHCO_3$ solution and Brine. The organic layers were finally dried over anhydrous $Na_2SO_4$. After filtration, the filtrate was evaporated under vacuum to give a mixture of starting material and compound 1 with a ratio by NMR of 1:14 (10.37 g) as a white foam. This mixture was used without purification in the next step.

Rf (Cyclohexane/Ethyl Acetate 6:4): 0.13.
HRMS ($ESI^+$): $[M+Na]^+$ ($C_{14}H_{20}O_{10}Na^+$) Calc. 371.0949, found 371.0941.
Compound 1α:
$^1$H-NMR (500 MHz, $CDCl_3$) δ: 5.50 (br d, 1H, $J_{1,2}$ 3.5 Hz, H-1); 5.45 (dd, 1H, $J_{3,4}$ 3.3, $J_{4,5}$ 1.4 Hz, H-4); 5.39 (dd, 1H, $J_{3,2}$ 10.8, $J_{3,4}$ 3.3 Hz, H-3); 5.14 (dd, 1H, $J_{2,3}$ 10.8, $J_{1,2}$ 3.5 Hz, H-2); 4.45 (ddd, 1H, $J_{5,6b}$ 6.7, $J_{5,6a}$ 6.5, $J_{5,4}$ 1.4 Hz, H-5); 4.10 (dd, 1H, $J_{6a,6b}$ 11.4, $J_{6a,5}$ 6.5 Hz, H-6a); 4.06 (dd, 1H, $J_{6a,6b}$ 11.4, $J_{6b,5}$ 6.7 Hz, H-6b); 3.12-3.02 (br s, 1H, OH); 2.12, 2.08, 2.03, 1.97 (4 s, 12H, 4 $COCH_3$).

$^{13}$C-NMR (125 MHz, CDCl$_3$) δ: 170.7, 170.6, 170.4, 170.2 (4 C=O); 90.9 (C-1); 68.5 (C-2); 68.4 (C-4); 67.4 (C-3); 66.5 (C-5); 62.0 (C-6); 21.0-20.7 (4 COCH$_3$).

Compound 1β:

$^1$H-NMR (500 MHz, CDCl$_3$) δ: 5.39-5.37 (br s, 1H, H-4); 5.06-5.04 (m, 2H, H-2, H-3); 4.70-4.65 (br s, 1H, H-1); 4.13 (d, 2H, J$_{5,6}$ 6.6 Hz, 2H-6); 3.93 (td, 1H, J$_{5,6}$ 6.6, J$_{5,4}$ 1.1 Hz, H-5); 3.62-3.55 (br s, 1H, OH); 2.14, 2.08, 2.02, 1.98 (4 s, 12H, 4 COCH$_3$).

$^{13}$C-NMR (125 MHz, CDCl$_3$) δ: 170.7, 170.6, 170.4, 170.2 (4 C=O); 96.3 (C-1); 71.4, 71.3, 70.5 (C-2, C-3, C-5); 67.4 (C-4); 61.7 (C-6); 21.1-20.7 (4 COCH$_3$).

The final product 11 was obtained with an overall yield of 8 mol % and with a high purity of more than 95% by NMR analysis.

uct of interest 11 with an overall yield of 8 mol %, with a purity of more than 95% by NMR analysis One skilled in the art will understand that various variations of the conditions of reaction of the invention can be made without departing from the core of the invention, including variations of the concentrations, nature of solvents, temperature, pressure, duration of reaction and stirring. Therefore, the invention covers all technical equivalents of the invention defined by the claims.

REFERENCES CITED

[1] C. Huo, C. Wang, M. Zhao, S. Peng, *Chem. Res. Toxicol.*, 2004, 17 (8), 1112-1120.

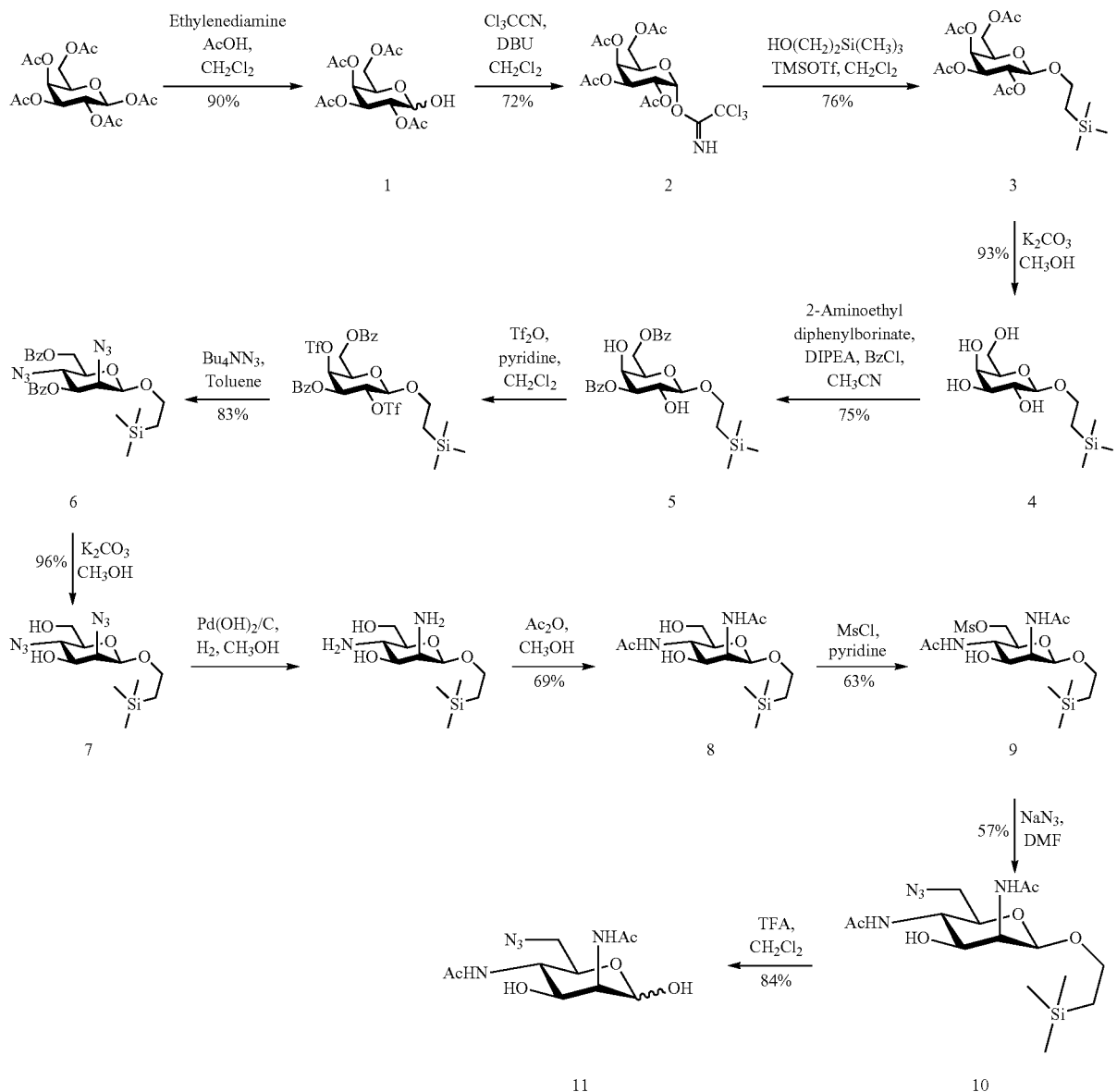

Scheme 1

The invention synthesis starts from the commercially available D-galactose pentaacetate and is providing the prod-

[2] W. Pilgrim, P. V. Murphy, *J. Org. Chem.*, 2010, 75, 6747-6755.

[3] E. Durantie, C. Bucher, R. Gilmour, *Chem. Eur. J.*, 2012, 18, 8208-8215.
[4] J. J. Plattner, R. G. Gless, H. Rapoport, *J. Am. Chem. Soc.*, 1972, 94, 8613.
[5] D. Lee, M. S. Taylor, *J. Am. Chem. Soc.*, 2011, 133, 3724-3727.
[6] Y. E. Tsvetkov, A. S. Shashkov, Y. A. Knirel, U. Zahringer, *Carbohydr. Res.*, 2001, 335, 221-243.
[7] J. Mas Pons, A. Dumont, G. Sautejeau, E. Fugier, A. Baron, S. Dukan, B. Vauzeilles, *Angew. Chem. Int. Ed.*, 2014, 53, 1275-1278.
[8] K. Jansson, T. Frejd, J. Kihlberg, G. Magnusson, *Tetrahedron Lett.*, 1988, 29, 361-362.

The invention claimed is:

1. A method of making 6-azido-2,4-diacetamido-2,4,6-trideoxy-D-mannose:

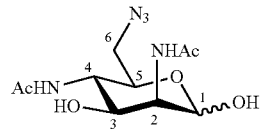

comprising reacting a compound of formula X:

formula X

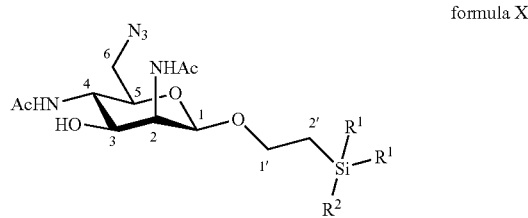

wherein $R^1$ is $C_1$ to $C_6$ alkyl or aryl, each of these groups being substituted or unsubstituted, and $R^2$ is substituted or unsubstituted $C_1$ to $C_6$ alkyl;
with a deprotecting reagent comprising a Lewis or Brönsted acid in a polar aprotic solvent, thereby obtaining a free C-1 OH group.

2. The method according to claim 1, wherein the compound of formula X is 1'-trimethylsilylethanyl 6-azido-2,4-diacetamido-2,4,6-trideoxy-β-D-mannopyranoside:

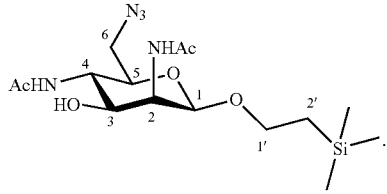

3. The method according to claim 1, wherein the compound of formula X is made by reacting a compound of formula IX:

formula IX

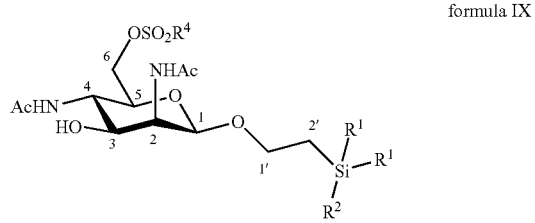

wherein $R^1$ is $C_1$ to $C_6$ alkyl or aryl, each of these groups being substituted or unsubstituted; $R^2$ is substituted or unsubstituted $C_1$ to $C_6$ alkyl; and $R^4$ is $C_1$ to $C_6$ alkyl, perfluoroalkyl or aryl, each of these groups being substituted or unsubstituted;
with an azide formation reagent comprising an organic or inorganic azide salt in a non-polar solvent or in a polar aprotic solvent, thereby obtaining a 6-azido group.

4. The method according to claim 3, wherein the compound of formula IX is 1'-trimethylsilylethanyl 2,4-diacetamido-2,4-dideoxy-6-O-mesyl-β-D-mannopyranoside:

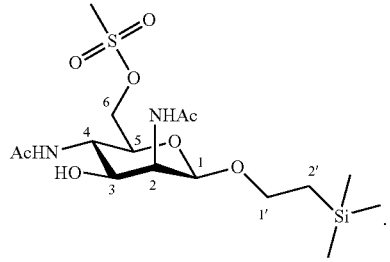

5. The method according to claim 3, wherein the compound of formula IX is made by reacting a compound of formula VIII:

formula VIII

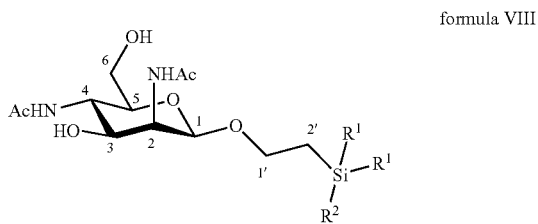

wherein $R^1$ is $C_1$ to $C_6$ alkyl or aryl, each of these groups being substituted or unsubstituted, and $R^2$ is substituted or unsubstituted $C_1$ to $C_6$ alkyl;
with a sulfonyl chloride or sulfonic anhydride in the presence of a base, with or without an organic solvent.

6. The method according to claim 5, wherein the compound of formula VIII is 1'-trimethylsilylethanyl 2,4-diacetamido-2,4-dideoxy-β-D-mannopyranoside:

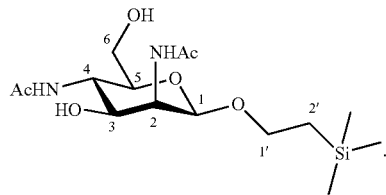

7. The method according to claim 5, wherein the compound of formula VIII is made by reacting a compound of formula VII:

formula VII

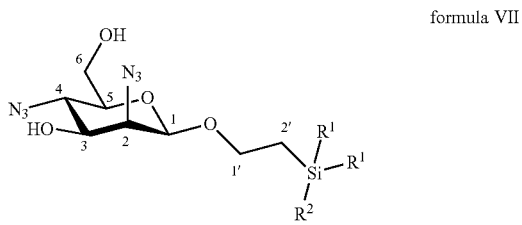

wherein $R^1$ is $C_1$ to $C_6$ alkyl or aryl, each of these groups being substituted or unsubstituted, and $R^2$ is substituted or unsubstituted $C_1$ to $C_6$ alkyl;

in a protic solvent, with a reagent for the reduction of azido groups, then reacting the intermediate product obtained with an acylating reagent.

8. The method according to claim 7, wherein the compound of formula VII is 1'-trimethylsilylethanyl 2,4-diazido-2,4-dideoxy-β-D-mannopyranoside:

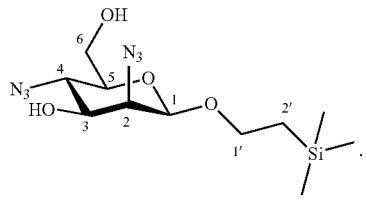

9. The method according to claim 7, wherein the compound of formula VII is made by reacting a compound of formula VI:

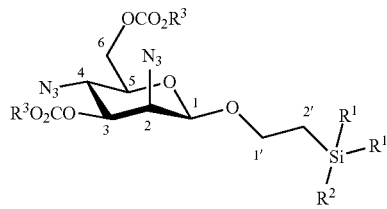

formula VI wherein $R^1$ and $R^3$ are $C_1$ to $C_6$ alkyl or aryl, each of these groups being substituted or unsubstituted, and $R^2$ is substituted or unsubstituted $C_1$ to $C_6$ alkyl;

in a protic solvent by using a reagent for deprotection of ester groups.

10. The method according to claim 9, wherein the reagent for deprotection of ester groups is sodium methanolate or potassium carbonate.

11. The method according to claim 9, wherein the compound of formula VI is made by reacting a compound of formula V:

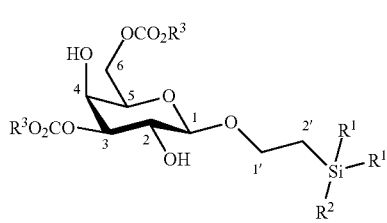

formula V wherein $R^1$ and $R^3$ are $C_1$ to $C_6$ alkyl or aryl, each of these groups being substituted or unsubstituted, and $R^2$ is substituted or unsubstituted $C_1$ to $C_6$ alkyl;

with an azido providing reagent, after adding to the organic solution, sulfonyl chloride or sulfonic anhydride in the presence of a base in a polar aprotic solvent.

12. The method according to claim 11, wherein the compound of formula V is made by reacting a compound of formula IV:

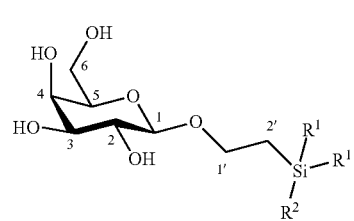

formula IV wherein $R^1$ is $C_1$ to $C_6$ alkyl or aryl, each of these groups being substituted or unsubstituted, and $R^2$ is substituted or unsubstituted $C_1$ to $C_6$ alkyl;

with 2-aminoethyl diphenylborinate or bis(tributyltin)oxide and an acyl chloride in a polar aprotic solvent in the presence of a base.

13. The method according to claim 12, wherein the compound of formula IV is made by reacting a compound of formula III:

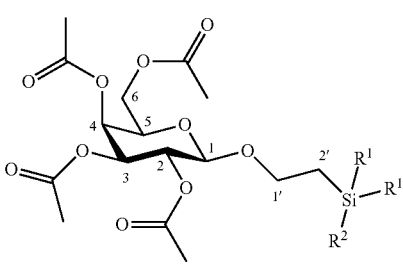

formula III wherein $R^1$ is $C_1$ to $C_6$ alkyl or aryl, each of these groups being substituted or unsubstituted, and $R^2$ is substituted or unsubstituted $C_1$ to $C_6$ alkyl;

in a protic solvent, in the presence of a reagent for the deprotection of ester groups.

14. The method according to claim 13, wherein the reagent for deprotection of ester groups is sodium methanolate or potassium carbonate.

15. The method according to claim 13, wherein the compound of formula III is made by reacting O-(2,3,4,6-tetra-O-acetyl-β-D-galactopyranosyl)trichloroacetimidate:

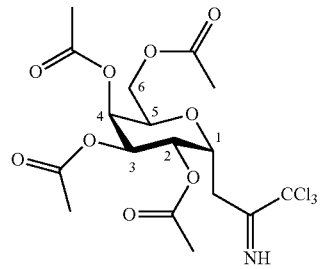

with a primary alcohol bearing a silyl group in the presence of a Lewis acid in a polar aprotic solvent.

16. The method according to claim 15, wherein the 0-(2,3,4,6-tetra-O-acetyl-β-D-alactopyranosyl) trichloroacetimidate is made by reacting 2,3,4,6-tetra-O-acetyl-D-galactopyranose:

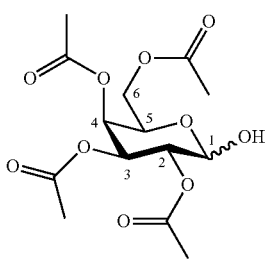

with an imidate introducing reagent, in the presence of a base in a polar aprotic solvent.

17. A method of making 6-azido-2,4-diacetamido-2,4,6-trideoxy-d-mannose:

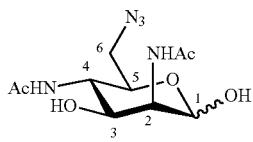

from commercially available d-galactose pentaacetate or D-galactose tetraacetate or tetraacetyl D-galactosyl trichloroacetimidate, according to the following reaction steps:

18. A compound selected from the group consisting of:

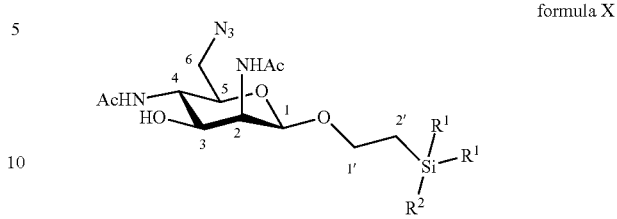

wherein $R^1$ is $C_1$ to $C_6$ alkyl or aryl, each of these groups being substituted or unsubstituted, and $R^2$ is substituted or unsubstituted $C_1$ to $C_6$ alkyl; and

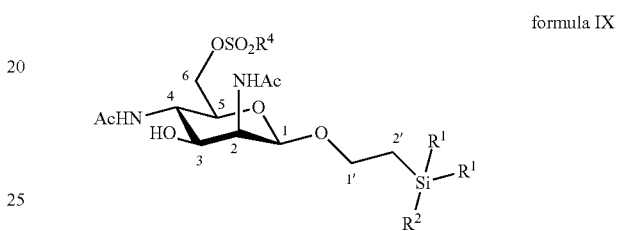

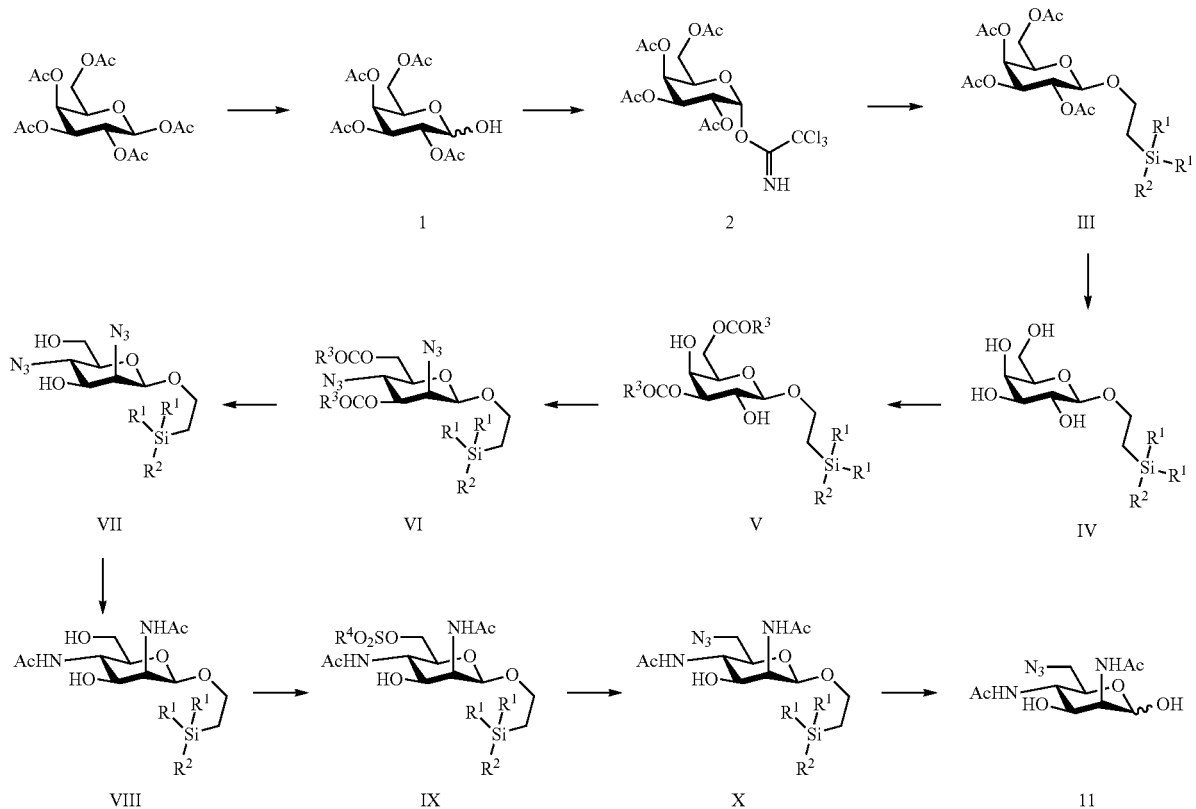

wherein $R^1$ and $R^3$ are $C_1$ to $C_6$ alkyl or aryl, each of these groups being substituted or unsubstituted; $R^2$ is substituted or unsubstituted $C_1$ to $C_6$ alkyl; and $R^4$ is $C_1$ to $C_6$ alkyl, perfluoroalkyl or aryl, each of these groups being substituted or unsubstituted.

wherein $R^1$ is $C_1$ to $C_6$ alkyl or aryl, each of these groups being substituted or unsubstituted; $R^2$ is substituted or unsubstituted $C_1$ to $C_6$ alkyl; and $R^4$ is $C_1$ to $C_6$ alkyl, perfluoroalkyl or aryl, each of these groups being substituted or unsubstituted.

19. A compound of formula VIII:

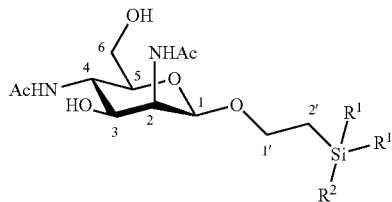

formula VIII wherein R¹ is $C_1$ to $C_6$ alkyl or aryl, each of these groups being substituted or unsubstituted, and R² is substituted or unsubstituted $C_1$ to $C_6$ alkyl.

20. A compound selected from the group consisting of:

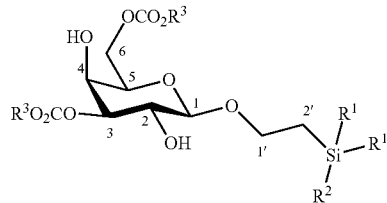

formula VI

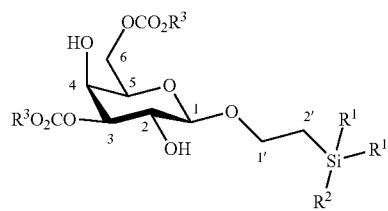

formula V wherein R¹ and R³ are $C_1$ to $C_6$ alkyl or aryl, each of these groups being substituted or unsubstituted, and R² is substituted or unsubstituted $C_1$ to $C_6$ alkyl; and wherein R¹ and R³ are $C_1$ to $C_6$ alkyl or aryl, each of these groups being substituted or unsubstituted, and R² is substituted or unsubstituted $C_1$ to $C_6$ alkyl.

* * * * *